United States Patent
Bernardon et al.

(10) Patent No.: US 7,122,564 B2
(45) Date of Patent: Oct. 17, 2006

(54) BIAROMATIC LIGAND ACTIVATORS OF PPARγ RECEPTORS

(75) Inventors: Jean-Michel Bernardon, Nice (FR); Laurence Clary, St. Laurent du Var (FR); Eric Terranova, Magagnosc (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 11/042,212

(22) Filed: Jan. 26, 2005

(65) Prior Publication Data

US 2005/0137238 A1    Jun. 23, 2005

Related U.S. Application Data

(62) Division of application No. 10/326,054, filed on Dec. 23, 2002, now Pat. No. 6,908,939.

(60) Provisional application No. 60/351,425, filed on Jan. 28, 2002.

(30) Foreign Application Priority Data

Dec. 21, 2001  (FR) ................... 01 16750
Mar. 1, 2002   (FR) ................... 02 02647

(51) Int. Cl.
*A01N 43/40* (2006.01)
(52) U.S. Cl. ............... 514/357; 514/438; 514/461; 514/507; 546/329; 549/83; 549/505; 560/19
(58) Field of Classification Search ........... 514/357, 514/438, 461, 507; 546/329; 549/83, 505; 560/19
See application file for complete search history.

(56) References Cited

U.S. PATENT DOCUMENTS 6,908,939 B1 *  6/2005  Bernardon et al. ......... 514/369

FOREIGN PATENT DOCUMENTS

| EP | 1 067 109 A1 | 1/2001 |
|---|---|---|
| FR | 2 812 876 A1 | 2/2002 |
| WO | WO 01/14349 A1 | 3/2001 |
| WO | WO 02/098840 A1 | 12/2002 |

OTHER PUBLICATIONS

Nomura et al., "(3-Substituted Benzyl)Thiazolidine-2,4-diones as Structurally New Antihyperglycemic Agents," 9(4) Bioorganic & Medicinal Chemistry Letters, 533-538 (Feb. 22, 1999) Elsevier Science Ltd.
French Search Report, issued for FR 01/16750 on Aug. 16, 2002, 2 pages.
Ishihara et al., 2000, CAS:133:58799.

* cited by examiner

*Primary Examiner*—Kamal A. Saeed
*Assistant Examiner*—Susannah L. Chung
(74) *Attorney, Agent, or Firm*—Buchanan Ingersoll & Rooney, PC

(57) ABSTRACT

Novel pharmaceutical/cosmetic compositions contain at least one biaromatic ligand activator of a PPARγ receptor, such biaromatic ligand having the structural formula (I):

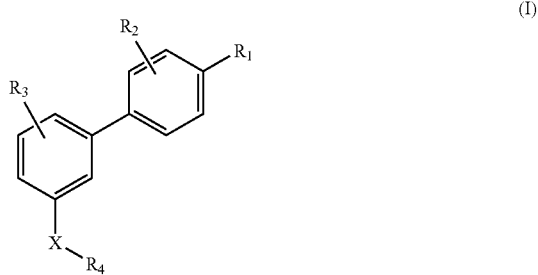

Figure 1:
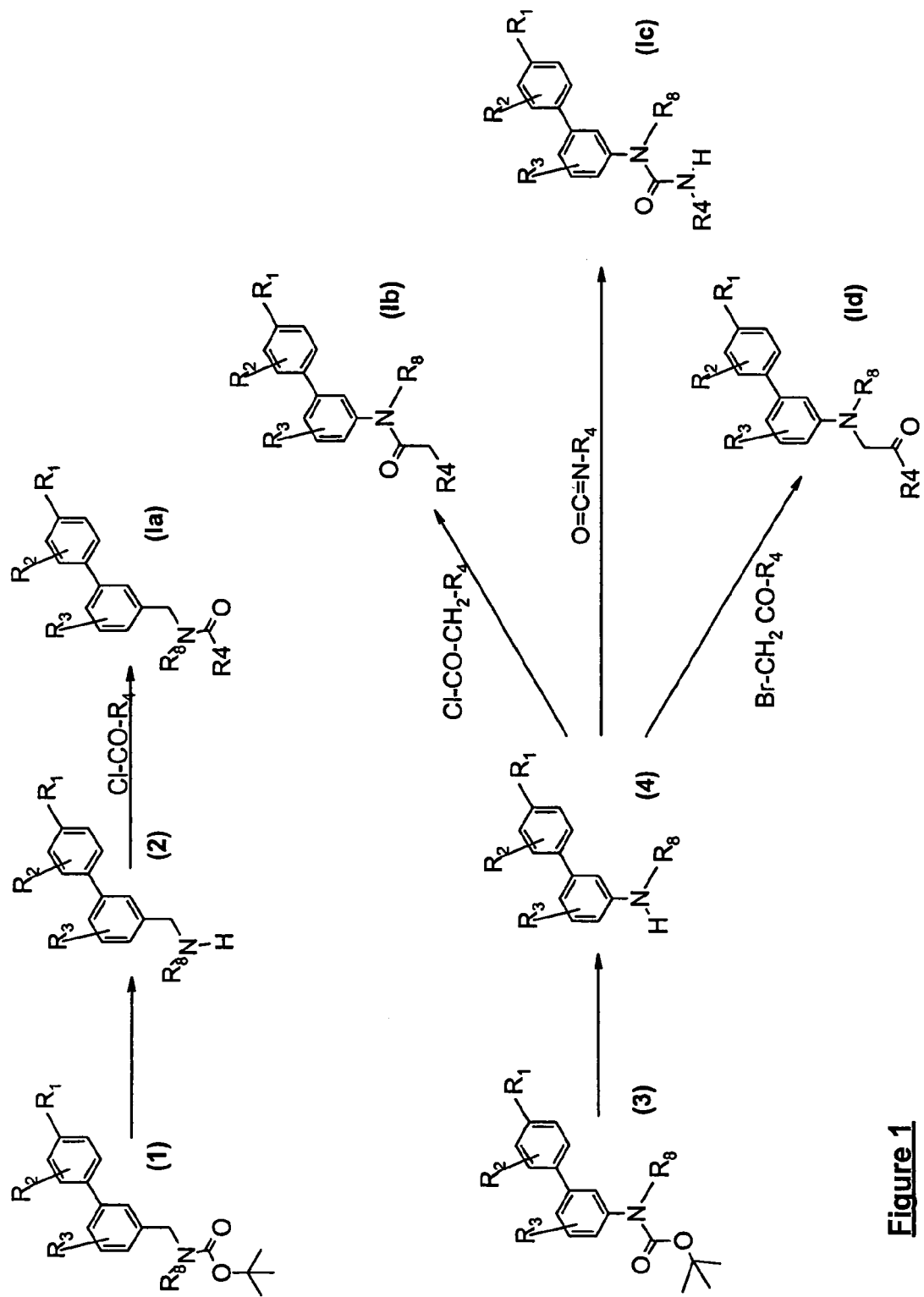

and are well suited, inter alia, for regulating and/or restoring skin lipid metabolism, for treating a wide variety of dermatological afflictions, and for preventing and/or treating the signs of aging and/or dry skin.

18 Claims, 2 Drawing Sheets

BIAROMATIC LIGAND ACTIVATORS OF PPARγ RECEPTORS

CROSS-REFERENCE TO PRIORITY/PROVISIONAL APPLICATIONS

This application is a divisional of parent U.S. patent application Ser. No. 10/326,054, filed Dec. 23, 2002, now U.S. Pat. No. 6,908,939 B2, which claims priority under 35 U.S.C. § 119 of FR-01/16750, filed Dec. 21, 2001, of FR-02/02647, filed Mar. 1, 2002, and of U.S. provisional application No. 60/351,425, filed Jan. 28, 2002, each hereby expressly incorporated by reference.

BACKGROUND OF THE INVENTION

1. Technical Field of the Invention

The invention relates, as novel and useful industrial products, to biaromatic compounds which are activators of receptors of the Peroxisome Proliferator-Activated Receptor type of subtype γ (PPARγ). It also relates to their method of preparation and to their use in pharmaceutical compositions for use in human or veterinary medicine, or alternatively in cosmetic compositions.

2. Description of the Prior Art

The activity of the PPAR-type receptors has been the subject of numerous studies. There may be mentioned, as a guide, the publication entitled "Differential Expression of Peroxisome Proliferator-Activated Receptor Subtypes During the Differentiation of Human Keratinocytes", Michel Rivier et al., J. Invest. Dermatol 111, 1998, p. 1116–1121, in which a large number of bibliographic references relating to PPAR-type receptors is listed. There may also be mentioned, as a guide, the dossier entitled "The PPARs: From orphan receptors to Drug Discovery", Timothy M. Willson, Peter J. Brown, Daniel D. Sternbach, and Brad R. Henke, J. Med. Chem., 2000, Vol. 43, p. 527–550.

The PPAR receptors activate transcription by binding to elements of DNA sequences, called peroxisome proliferator response elements (PPRE), in the form of a heterodimer with the retinoid X receptors (called RXRs).

Three human PPAR subtypes have been identified and described: PPARα, PPARγ and PPARδ (or NUC1).

PPARα is mainly expressed in the liver while PPARδ is ubiquitous.

PPARγ is the most widely studied of the three subtypes. All the references suggest a critical role of the PPARγ receptors in the regulation of differentiation of adipocytes, where it is highly expressed. It also plays a key role in systemic lipid homeostasis.

It has in particular been described in Patent Application WO 96/33724 that PPARγ-selective compounds, such as prostaglandin-J2 or -D2, are potential active agents for treating obesity and diabetes.

Moreover, the applicant has already described in Patent Application FR98/02894 the use of PPARγ-activating compounds in the preparation of a pharmaceutical composition, the composition being intended for treating skin disorders linked to an abnormality of differentiation of epidermal cells.

SUMMARY OF THE INVENTION

One of the aims of the present invention is to provide novel PPARγ-activating compounds exhibiting a better biological activity than the prior art compounds.

Thus, the present invention relates to biaromatic compounds corresponding to the following general formula:

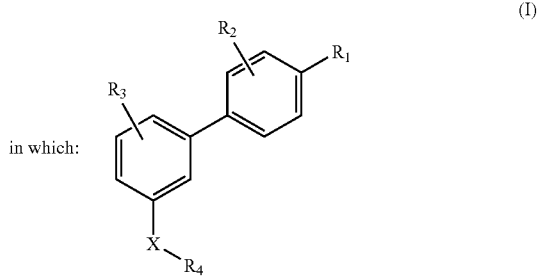

(I)

in which:

$R_1$ represents a radical of the following formulae (a) or (b):

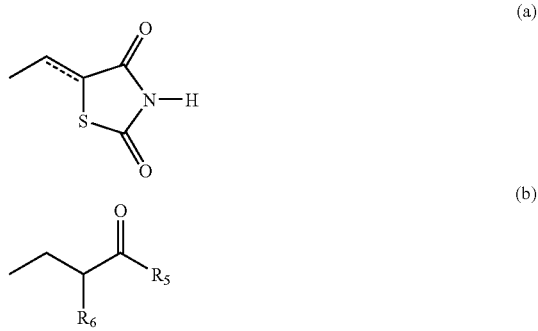

$R_5$ and $R_6$ having the meanings given below, $R_2$ and $R_3$, which may be identical or different, represent a hydrogen atom, an alkyl radical having from 1 to 6 carbon atoms, an aryl radical, a halogen atom, a radical —$OR_7$, a polyether radical, a nitro radical or an amino radical which may be optionally substituted with alkyl radicals having from 1 to 6 carbon atoms;

$R_7$ having the meaning given below,

X represents the bonds having the following structures:
—$CH_2$—$N(R_8)$—CO—
—$N(R_8)$—CO—$N(R_9)$—
—$N(R_8)$—CO—$CH_2$—
—$N(R_8)$—$CH_2$—CO— which may be read from left to right or conversely $R_8$ and $R_9$ having the meanings given below, $R_4$ represents:
- a phenyl, benzyl, phenethyl, thienyl, furyl or pyridyl radical, all these radicals being substituted with a group $R_{10}$,
  $R_{10}$ having the meanings given below,
- a pyrrolyl, pyrazinyl, naphthyl, biphenyl, indolyl, indenyl, benzothienyl, benzofuryl, benzothiazolyl or quinolyl radical, it being possible for all these radicals to be mono- or disubstituted with a group $R_{11}$ and/or $R_{12}$,
  $R_{11}$ and $R_{12}$ having the meanings given below,
- a radical —$(CH_2)n$-$(CO)_qR_{13}$,
  n, q and $R_{13}$ having the meanings given below,
- an adamantyl, diphenylmethyl, diphenylethyl, diphenylpropyl, diphenylbutyl, cyclopropylmethyl, cyclopentylethyl, 2-benzimidazolyl-ethyl, cyclohexylmethyl, phenoxyphenyl, 9H-fluorenyl, benzyloxyphenyl, 4-heptyloxyphenyl, or 4-(6-methyl-2-benzothiazolyl)phenyl radical,
a radical —$(CH_2)n$-O—$R_{13}$,
n and $R_{13}$ having the meanings given below,
$R_5$ represents a hydroxyl radical or an alkoxy radical having from 1 to 9 carbon atoms,
$R_6$ represents an alkyl radical having from 1 to 6 carbon atoms, a radical $OR_{14}$ or a radical $SR_{14}$,
$R_{14}$ having the meanings given below,
$R_7$ represents a hydrogen atom, an alkyl radical having from 1 to 6 carbon atoms, an aryl radical or an aralkyl radical,
$R_8$ represents a hydrogen atom or an alkyl radical having from 1 to 6 carbon atoms,
$R_9$ represents a hydrogen atom or an alkyl radical having from 1 to 6 carbon atoms,
$R_{10}$ represents:
   a radical —$S(O)_m R_{15}$
   a radical —$(CH_2)p$-$COR_{16}$
   a radical —O—$R_{17}$
   m, p, $R_{15}$, $R_{16}$ and $R_{17}$ having the meanings given below,
$R_{11}$ and $R_{12}$ represent a halogen atom, a radical $CF_3$, an alkyl radical having from 1 to 12 carbon atoms, an alkoxy radical having from 1 to 9 carbon atoms, a polyether radical, a nitro functional group, a hydroxyl radical optionally protected by an acetyl or benzoyl group, an amino functional group optionally substituted with at least one alkyl having from 1 to 12 carbon atoms or with a radical —CONH—$R_{24}$, or protected by an acetyl or benzoyl group, a radical —$S(O)_m R_{15}$, a radical $(CH_2)p$-$COR_{16}$ or a radical —$OR_{17}$,
m, p, $R_{15}$, $R_{16}$, $R_{17}$ and $R_{24}$ having the meanings given below,
n may take the values ranging from 1 to 9,
q may take the values 0 or 1,
$R_{13}$ represents a radical —$OR_{18}$, a radical —$N(R_{19})(R_{20})$, an aryl radical, an aralkyl radical or a heteroaryl radical,
$R_{18}$, $R_{19}$ and $R_{20}$ having the meanings given below,
m may take the values 0, 1 or 2,
p may take the values 0, 1 or 2,
$R_{14}$ represents an alkyl radical having from 1 to 12 carbon atoms, a radical $CF_3$, an aryl radical or an aralkyl radical,
$R_{15}$ represents an alkyl radical having from 1 to 12 carbon atoms, an aryl radical or an aralkyl radical,
$R_{16}$ represents an alkyl radical having from 1 to 12 carbon atoms, a radical
—$OR_{21}$, a radical —$N(R_{22})(R_{23})$, an aryl radical or an aralkyl radical,
$R_{21}$, $R_{22}$ and $R_{23}$ having the meanings given below,
$R_{17}$ represents an aryl radical or an aralkyl radical,
$R_{18}$ represents a hydrogen atom or an alkyl radical having from 1 to 12 carbon atoms,
$R_{19}$ and $R_{20}$, which may be identical or different, represent a hydrogen atom, an alkyl radical having from 1 to 12 carbon atoms, or taken together may form a heterocycle,
$R_{21}$ represents a hydrogen atom or an alkyl radical having from 1 to 12 carbon atoms,
$R_{22}$ and $R_{23}$, which may be identical or different, represent a hydrogen atom, an alkyl radical having from 1 to 12 carbon atoms, or taken together may form a heterocycle,
$R_{24}$ represents a phenyl, diphenylmethyl, diphenylpropyl, diphenylbutyl, biphenylyl, phenoxyphenyl, 9H-fluorenyl, 4-benzyloxyphenyl, 4-heptyloxyphenyl, or 4-(6-methyl-2-benzothiazolyl)phenyl radical, and the salts of the compounds of formula (I) when $R_1$ contains a carboxylic acid functional group and the optical and geometric isomers of the said compounds of formula (I).

The present invention also relates to the salts of the compounds of formula (I) when $R_1$ contains a carboxylic acid functional group and the optical and geometric isomers of the said compounds of formula (I).

DETAILED DESCRIPTION OF BEST MODE AND SPECIFIC/PREFERRED EMBODIMENTS OF THE INVENTION

When the compounds according to the invention are provided in the form of a salt, this is preferably a salt of an alkali or alkaline-earth metal, or alternatively a zinc salt or salts of an organic amine.

According to the present invention:

The expression alkyl radical having from 1 to 6 carbon atoms is preferably understood to mean the methyl, ethyl, isopropyl, butyl, tert-butyl and hexyl radicals.

The expression alkyl radical having from 1 to 12 carbon atoms is preferably understood to mean the methyl, ethyl, isopropyl, butyl, tert-butyl, hexyl, octyl, decyl and dodecyl radicals.

The expression polyether radical is preferably understood to mean a radical having from 1 to 6 carbon atoms interrupted by at least one oxygen atom such as the methoxymethoxy, ethoxymethoxy and methoxyethoxymethoxy radicals.

The expression halogen atom is preferably understood to mean a fluorine, chlorine or bromine atom.

The expression alkoxy radical having from 1 to 9 carbon atoms is preferably understood to mean the methoxy, ethoxy, isopropyloxy, tert-butoxy and hexyloxy radicals.

The expression aryl radical is preferably understood to mean a phenyl, biphenyl, cinnamyl or naphthyl radical which may be mono- or disubstituted with a halogen atom, a radical $CF_3$, an alkyl radical having from 1 to 12 carbon atoms, an alkoxy radical having from 1 to 7 carbon atoms, a nitro functional group, a polyether radical, an aryl radical, a benzoyl radical, an alkyl ester group, a carboxylic acid, a hydroxyl radical optionally protected by an acetyl or benzoyl group or an amino functional group optionally protected by an acetyl or benzoyl group or optionally substituted with at least one alkyl having from 1 to 12 carbon atoms.

The expression aralkyl radical is preferably understood to mean a benzyl or phenethyl radical which may be mono- or disubstituted with a halogen atom, a radical $CF_3$, an alkyl radical having from 1 to 12 carbon atoms, an alkoxy radical having from 1 to 6 carbon atoms, a nitro functional group, a polyether radical, a hydroxyl radical optionally protected by an acetyl or benzoyl group or an amino functional group optionally protected by an acetyl or benzoyl group or optionally substituted with at least one alkyl having from 1 to 12 carbon atoms.

The expression heteroaryl radical is preferably understood to mean an aryl radical interrupted by one or more heteroatoms, such as the pyridyl, furyl, thienyl, isoxazolyl, oxadiazolyl, oxazolyl, benzimidazole, indolyl or benzofuran radical, optionally substituted with at least one halogen, an alkyl having from 1 to 12 carbon atoms, an alkoxy having from 1 to 7 carbon atoms, an aryl radical, a nitro functional group, a polyether radical, an aryl radical, a benzoyl radical, an alkyl ester group, a carboxylic acid, a hydroxyl optionally protected by an acetyl or benzoyl group or an amino functional group optionally protected by an acetyl or benzoyl group or optionally substituted with at least one alkyl having from 1 to 12 carbon atoms.

The expression heterocycle is preferably understood to mean the morpholino, piperidino, piperazino, 2-oxopiperidin-1-yl and 2-oxopyrrolidin-1-yl radicals optionally substituted with at least one alkyl group having from 1 to 12 carbon atoms, an alkoxy having from 1 to 7 carbon atoms, an aryl radical, a nitro functional group, a polyether radical, an aryl radical, a benzoyl radical, an alkyl ester group, a carboxylic acid, a hydroxyl optionally protected by an acetyl or benzoyl group or an amino functional group optionally protected by an acetyl or benzoyl group or optionally substituted with at least one alkyl having from to 1 to 12 carbon atoms.

Among the compounds corresponding to the above general formula (I), the following may be mentioned, alone or as a mixture:

1-methyl 7-{[4'-(2,4-dioxothiazolidin-5-ylmethyl)-biphenyl-3-ylmethyl]methylcarbamoyl}heptanoate;
2-methyl 9-{[4'-(2,4-dioxothiazolidin-5-ylmethyl)-biphenyl-3-ylmethyl]methylcarbamoyl}nonanoate;
3-methyl N-[4'-(2,4-dioxothiazolidin-5-ylmethyl)-biphenyl-3-ylmethyl]-N-methylterephthalamate;
4-3-cyclopentyl-N-[4'-(2,4-dioxothiazolidin-5-ylmethyl)biphenyl-3-ylmethyl]-N-methylpropionamide;
5-N-[4'-(2,4-dioxothiazolidin-5-ylmethyl)biphenyl-3-ylmethyl]-N-methylnaphthalene-1-carboxamide;
6-N-[4'-(2,4-dioxothiazolidin-5-ylmethyl)biphenyl-3-ylmethyl]-N-methylnaphthalene-2-carboxamide;
7-N-[4'-(2,4-dioxothiazolidin-5-ylmethyl)biphenyl-3-ylmethyl]-N-methyl-2-phenoxyacetamide;
8-N-[4'-(2,4-dioxothiazolidin-5-ylmethyl)biphenyl-3-ylmethyl]-N-methyl-1-methyl-1H-pyrrole-2-carboxamide;
9-N-[4'-(2,4-dioxothiazolidin-5-ylmethyl)biphenyl-3-ylmethyl]-N-methyladamantane-1-carboxamide;
10-N-[4'-(2,4-dioxothiazolidin-5-ylmethyl)biphenyl-3-ylmethyl]-N-methylbiphenyl-4-carboxamide;
11-N-[4'-(2,4-dioxothiazolidin-5-ylmethy)biphenyl-3-ylmethy1]-N-methylbenzo[b]thiophene-2-carboxamide;
12-N-[4'-(2,4-dioxothiazolidin-5-ylmethyl)biphenyl-3-ylmethyl]-N-methyl-6-oxo-6-phenylhexanamide;
13-4-dimethylamino-N-[4'-(2,4-dioxothiazolidin-5-yhnethyl)biphenyl-3-ylmethyl]-N-methylnaphthalene-1-carboxamide;
14-N-[4'-(2,4-dioxothiazolidin-5-ylmethyl)biphenyl-3-ylmethyl]-4-methanesulphonyl-N-methylbenzamide;
15-N-[4'-(2,4-dioxothiazolidin-5-ylmethyl)biphenyl-3-ylmethyl]-N-methyl-4-(1-phenylmethanoyl)benzamide;
16-6-(2-methoxyethoxymethoxy)-N-[4'-(2,4-dioxothiazolidin-5-ylmethyl)biphenyl-3-ylmethyl]-N-methylnaphthalene-2-carboxamide;
17-6-hydroxy-N-[4'-(2,4-dioxothiazolidin-5-ylmethyl)-biphenyl-3-ylmethyl]-N-methylnaphthalene-2-carboxamide;
18-N-[4'-(2,4-dioxothiazolidin-5-ylmethyl)biphenyl-3-ylmethyl]-N-methyl-4-methylsulphanylbenzamide;
19-(S)-3-(3'-{[(1-biphenyl-4-ylmethanoyl)methyl-amino]methyl}biphenyl-4-yl)-2-ethoxypropionic acid;
20-(S)-2-ethoxy-3-(3'-{[methyl-(6-oxo-6-phenylhexanoyl)amino]methyl}biphenyl-4-yl)propionic acid;
21-1-[4'-(2,4-dioxothiazolidin-5-ylmethyl)biphenyl-3-yl]-1-methyl-3-naphthalen-2-ylurea;
22-3-(4-dimethylaminophenyl)-1-[4'-(2,4-dioxothiazolidin-5-ylmethyl)biphenyl-3-yl]-1-methylurea;
23-(S)-2-ethoxy-3-{3'-[({1-[6-(2-methoxyethoxy-methoxy)naphthalen-2-yl]methanoyl}methylamino)methyl]-biphenyl-4-yl}propionic acid;
24-6-(methoxymethoxy)-N-[4'-(2,4-dioxothiazolidin-5-ylmethyl)biphenyl-3-ylmethyl]-N-methylnaphthalene-2-carboxamide;
25-6-(methoxycarbonyl)-N-[4'-(2,4-dioxothiazolidin-5-ylmethyl)biphenyl-3-ylmethyl]-N-methylnaphthalene-2-carboxamide;
26-6-(propyloxy)-N-[4'-(2,4-dioxothiazolidin-5-ylmethyl)biphenyl-3-ylmethyl]-N-methylnaphtahlene-2-carboxamide;
27-6-(hexyloxy)-N-[4'-(2,4-dioxothiazolidin-5-ylmethyl)biphenyl-3-ylmethyl]-N-methylnaphthalene-2-carboxamide;
28-6-(nonyloxy)-N-[4'-(2,4-dioxothiazolidin-5-ylmethyl)biphenyl-3-ylmethyl]-N-methylnaphthalene-2-carboxamide;
29-N-[4'-(2,4-dioxothiazolidin-5-ylmethyl)biphenyl-3-ylmethyl]-N-methyl-4'-propylbiphenyl-2-carboxamide;
30-N-[4'-(2,4-dioxothiazolidin-5-ylmethyl)biphenyl-3-ylmethyl]-N-methyl-4-phenoxybenzamide;
31-N-[4'-(2,4-dioxothiazolidin-5-ylmethyl)biphenyl-3-ylmethyl]-N-methyl-7-oxo-7-phenyltheptanamide;
32-(6-{[4'-(2,4-dioxothiazolidin-5-ylmethyl)biphenyl-3-ylmethyl]methylcarbamoyl}naphthalen-2-yloxy)acetic acid;
33-(6-{[4'-(2,4-dioxothiazolidin-5-ylmethyl)biphenyl-3-ylmethyl]methylcarbamoyl}naphthalen-2-yloxy)acetic acid methyl ester;
34-6-methoxy-N-[4'-(2,4-dioxothiazolidin-5-ylmethyl)biphenyl-3-ylmethyl]-N-methylnaphthalene-2-carboxamide;
35-6-acetoxy-N-[4'-(2,4-dioxothiazolidin-5-ylmethyl)biphenyl-3-ylmethyl]-N-methylnaphthalene-2-carboxamide;
36-6-amino-N-[4'-(2,4-dioxothiazolidin-5-ylmethyl)biphenyl-3-ylmethyl]-N-methylnaphthalene-2-carboxamide;
37-6-acetylamino-N-[4'-(2,4-dioxothiazolidin-5-ylmethyl)biphenyl-3-ylmethyl]-N-methylnaphthalene-2-carboxamide;
38-1-hydroxy-N-[4'-(2,4-dioxothiazolidin-5-ylmethyl)biphenyl-3-ylmethyl]-N-methylnaphthalene-2-carboxamide;
39-1-methoxy-N-[4'-(2,4-dioxothiazolidin-5-ylmethyl)biphenyl-3-ylmethyl]-N-methylnaphthalene-2-carboxamide;
40-6-bromo-N-[4'-(2,4-dioxothiazolidin-5-ylmethyl)biphenyl-3-ylmethyl]-N-methylnaphthalene-2-carboxamide;
41-6-carboxyl-N-[4'-(2,4-dioxothiazolidin-5-ylmethyl)biphenyl-3-ylmethyl]-N-methylnaphthalene-2-carboxamide;
42-6-carboxyl-N-[4'-(2,4-dioxothiazolidin-5-ylmethyl)biphenyl-3-ylmethyl]-N-methylnaphthalene-2-carboxamide methyl ester;
43-6-(3-phenylureido)-N-[4'-(2,4-dioxothiazolidin-5-ylmethyl)biphenyl-3-ylmethyl]-N-methylnaphthalene-2-carboxamide;
44-3-hydroxy-N-[4'-(2,4-dioxothiazolidin-5-ylmethyl)biphenyl-3-ylmethyi]-N-methylnaphthalene-2-carboxamide;
45-3-methoxy-N-[4'-(2,4-dioxothiazolidin-5-ylmethyl)biphenyl-3-ylmethyl]-N-methylnaphthalene-2-carboxamide;

46-N-[4'-(2,4-dioxothiazolidin-5-ylmethyl)biphenyl-3-ylmethyl]-N-methyl-4'-hydroxybiphenyl-4-carboxamide;
47-N-[4'-(2,4-dioxothiazolidin-5-ylmethyl)biphenyl-3-ylmethyl]-N-methyl-4'-methoxybiphenyl-4-carboxamide;
48-N-[4'-(2,4-dioxothiazolidin-5-ylmethyl)biphenyl-3-ylmethyl]-N-methyl-4'-propyloxybiphenyl-4-carboxamide;
49-N-[4'-(2,4-dioxothiazolidin-5-ylmethyl)biphenyl-3-ylmethyl]-N-methyl-4'-hexyloxybiphenyl-4-carboxamide;
50-N-[4'-(2,4-dioxothiazolidin-5-ylmethyl)biphenyl-3-ylmethyl]-N-methyl-4'-acetoxybiphenyl-4-carboxamide;
51-(4'-{[4'-(2,4-dioxothiazolidin-5-ylmethyl)biphenyl-3-ylmethyl]methylcarbamoyl}biphenyl-4-yloxy)acetic acid;
52-(4'-{[4'-(2,4-dioxothiazolidin-5-ylmethyl)biphenyl-3-ylmethyl]methylcarbamoyl}biphenyl-4-yloxy)acetic acid methyl ester;
53-N-[4'-(2,4-dioxothiazolidin-5-ylmethyl)biphenyl-3-ylmethyl]-N-methyl4'-methoxymethoxybiphenyl-4-carboxamide;
54-N-[4'-(2,4-dioxothiazolidin-5-ylmethyl)biphenyl-3-ylmethyl]-N-methyl-4'-nonyloxybiphenyl-4-carboxamide;
55-N-[4'-(2,4-dioxothiazolidin-5-ylmethyl)biphenyl-3-ylmethyl]-N-methyl4'-(2-methoxyethoxy)biphenyl-4-carboxamide;
56-3-biphenyl-4-yl-1-[4'-(2,4-dioxothiazolidin-5-ylmethyl)biphenyl-3-yl]-1-methylurea;
57-1-[4'-(2,4-dioxothiazolidin-5-ylmethyl)biphenyl-3-yl]-3-(9H-fluoren-2-yl)-1-methylurea;
58-1-[4'-(2,4-dioxothiazolidin-5-ylmethyl)biphenyl-3-yl]-3-(9H-fluoren-9-yl)-1-methylurea;
59-3-benzhydryl-1-[4'-(2,4-dioxothiazolidin-5-ylmethyl)biphenyl-3-yl]-1-methylurea;
60-1-[4'-(2,4-dioxothiazolidin-5-ylmethyl)biphenyl-3-yl]-1-methyl-3-(3-phenoxyphenyl)urea;
61-1-[4'-(2,4-dioxothiazolidin-5-ylmethyl)biphenyl-3-yl]-3-(4-heptyloxyphenyl)-1-methylurea;
62-3-(4-benzyloxyphenyl)-1-[4'-(2,4-dioxothiazolidin-5-ylmethyl)biphenyl-3-yl]-1-methylurea;
63-1-[4'-(2,4-dioxothiazolidin-5-ylmethyl)biphenyl-3-yl]-1-methyl-3-[4-(6-methylbenzothiazol-2-yl)phenyl]urea;
64-4-(2-methoxyethoxymethoxy)-N-[4'-(2,4-dioxothiazolidin-5-ylmethyl)biphenyl-3-ylmethyl]-N-methylbiphenyl-4-carboxamide;
65-4'-hydroxy-N-[4'-(2,4-dioxothiazolidin-5-ylmethyl)biphenyl-3-ylmethyl]-N-methylbiphenyl-4-carboxamide;
66-1-[4'-(2,4-dioxothiazolidin-5-ylmethyl)biphenyl-3-yl]-3-(4-hexyloxyphenyl)-1-methylurea.

According to the present invention, the more particularly preferred compounds of formula (I) are those for which:
  $R_1$ represents the radical of formula (a) or the radical of formula (b) where $R_5$ represents a hydroxyl radical and $R_6$ represents the radical $OR_{14}$ and/or
  X represents the linkage having the structure —$CH_2$—N($R_8$)—CO— or —N($R_8$)—CO—N($R_9$)— read from left to right or conversely.

Figure 2:
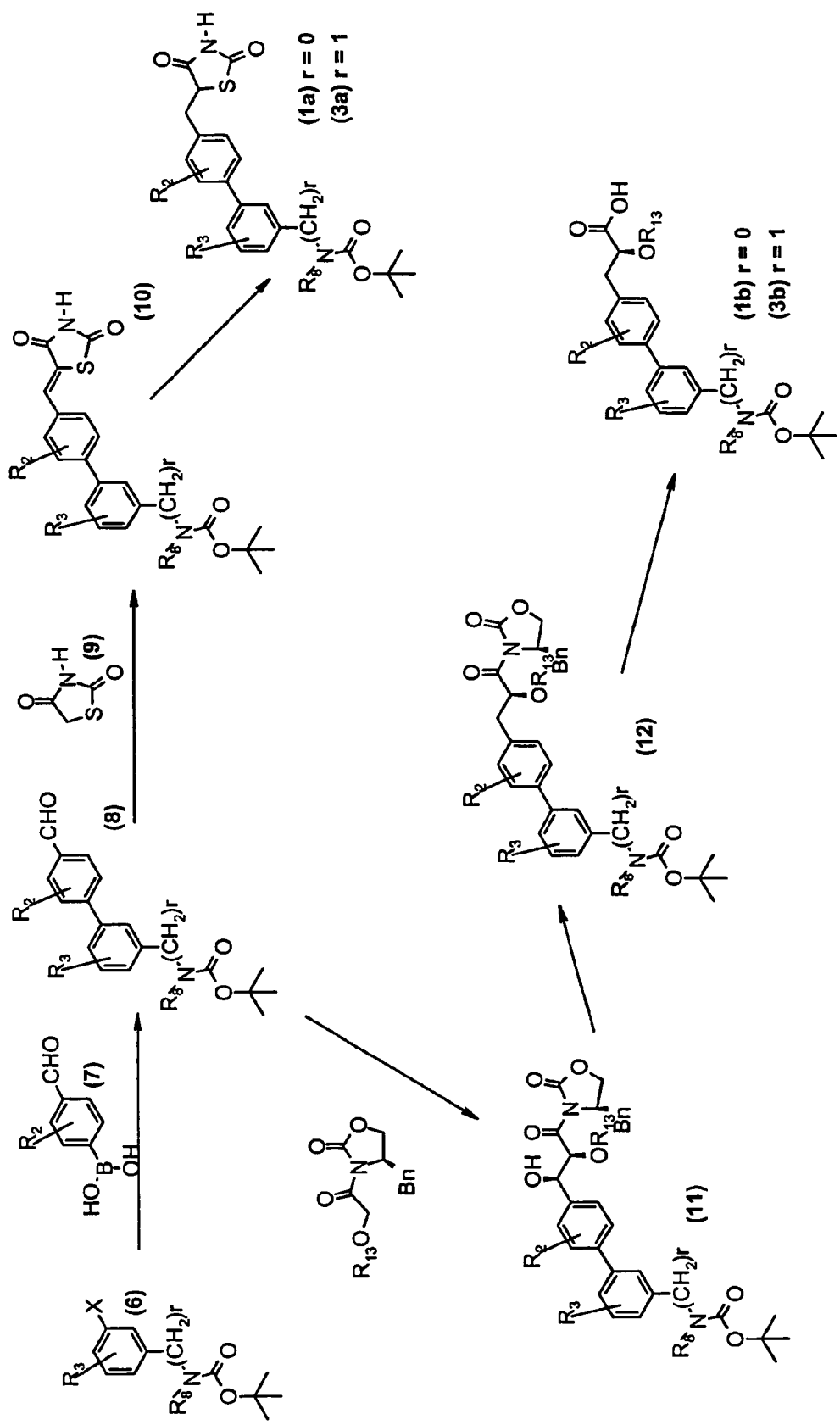

The subject of the present invention is also the methods for preparing the compounds of formula (I), in particular according to the reaction schemes given in FIGS. 1 and 2.

In FIG. 1, the derivatives of formula (Ia) and (Ib) may be obtained respectively from the derivatives (2) and (4) by acylation of the amine functional group with an activated form of a carboxylic acid, for example an acid chloride (Cl—CO—$R_4$), in the presence of a tertiary amine (for example triethylamine or pyridine) in an anhydrous solvent, preferably THF, it being possible for the derivatives (2) and (4) to be obtained respectively from the compounds (1) and (3) by deprotection of the amine functional group in the presence of trifluoroacetic anhydride or hydrochloric acid in a solvent such as THF or dichloromethane.

The derivatives of formula (Ic) may be obtained (FIG. 1) from the derivatives (4) by reaction with an isocyanate of formula O=C=N—$R_4$ in a solvent such as dichloromethane in the presence of a base such as triethylamine.

The derivatives of formula (Id) may be obtained (FIG. 1) from the derivatives (4) by reaction with an alpha-bromoketone (Br—$CH_2$—CO—$R_4$) in a solvent such as acetone or methyl ethyl ketone in the presence of a base such as potassium carbonate.

The derivatives (1a) and (3a) may be obtained (FIG. 2) from the compounds (10) either by hydrogenation in the presence of palladium on carbon or Raney nickel in a solvent such as ethyl acetate, dioxane, DMF or ethyl alcohol or by reduction in the presence of lithium borohydride and pyridine in THF. The compounds (10) may be obtained from the compounds (8) by reaction with 2,4-thiazolidinedione (9) in the presence of piperidine acetate in an alcoholic solvent such as ethanol or in toluene. The compounds (8) may be obtained from halogenated derivatives (6), preferably from iodinated or brominated derivatives, by a Suzuki type coupling reaction with a boronic acid (7). This reaction is carried out in the presence of a palladium catalyst, for example tetrakis(triphenylphosphine)-palladium according to the conditions described by N. Miyaura et al. Synthetic Communications (1981) 11(7), 513–519. The boronic derivatives (7) may be obtained from the corresponding halogenated (preferably iodinated or brominated) derivatives first of all by protection of the aldehyde functional group in acetal form and then conversion to a lithium compound, reaction with trimethyl or triisopropyl borate and hydrolysis in acidic medium (hydrochloric acid).

The halogenated derivatives (6) are obtained from the corresponding primary amines. The latter are protected by coupling with di-tert-butyl carbonate in a solvent such as dichloromethane. The resulting carbamate is alkylated via the use of a base such as sodium hydride and an alkyl halide in order to give the derivative (6). The derivatives (1b) and (3b) may be obtained (FIG. 2) from the derivatives (8) by a succession of reactions according to the conditions described by B. Hulin et al. J. Med. Chem. (1996) 39, 3897–3907.

When $R_1$ contains an acid functional group, the compounds are prepared by protecting $R_1$ with a protecting group of the alkyl, allyl, benzyl or tert-butyl type. The passage to the free form may be carried out:
  in the case of an alkyl protective group, by means of sodium hydroxide or lithium hydroxide in an alcoholic solvent such as methanol or in THF;
  in the case of an allyl protective group, by means of a catalyst such as some transition metal complexes in the presence of a secondary amine such as morpholine;
  in the case of a benzyl protective group, by debenzylation in the presence of hydrogen by means of catalyst such as palladium on carbon;
  in the case of a tert-butyl type protective group by means of trimethylsilane iodide.

The compounds according to the invention have PPARγ type receptor activating properties. The expression activator of PPARγ type receptors is understood to mean according to the invention any compound which exhibits a percentage activation of the PPARγ receptors of at least 20%, at the concentration of 1 µM, in a transactivation test as described in Example 35.

The preferred compounds of the present invention have a percentage activation of the PPARγ receptors greater than or equal to 40% and advantageously greater than or equal to 70%.

Preferably, the activator of the PPARγ type receptors is specific, that is to say that it has a ratio of the percentage activation of the PPARα receptors to the percentage activation of the PPARα receptors (calculated relative to a reference compound, Wy 14643, activating the PPARα receptors by 100%) greater than or equal to 3. Preferably, this ratio is greater than or equal to 5 and more advantageously greater than or equal to 10.

The affinity of the PPAR derivatives for the human PPARγ receptor was also determined in a binding test as described in Example 36. The expression ligand for the PPARγ receptors is understood to mean any compound according to the invention having a Kd value of less than 10 000 mM. Preferably, the compounds according to the invention have a Kd value of less than 1000 μM and advantageously less than 100 nM.

The subject of the present invention is also the compounds of formula (I) as described above, as a medicament.

The compounds according to the invention are particularly suitable in the fields of the following treatments:

1) for treating dermatological conditions linked to a keratinization disorder related to cell differentiation and proliferation, in particular to treat acne vulgaris, comedo-type acne, polymorphic acne, acne rosacea, nodulocystic acne, acne conglobata, senile acne, secondary acne such as solar acne, acne medicamentosa or occupational acne;
2) for treating other types of keratinization disorders, in particular ichtyosis, ichtyosiform states, Darrier's disease, keratosis palmaris et plantaris, leukoplasia and leukoplasiform states, cutaneous or mucosal (buccal) lichen;
3) for treating other dermatological conditions with an inflammatory immunoallergic component, with or without cell proliferation disorder, and in particular all the forms of psoriasis, whether cutaneous, mucosal or ungual, and even psoriatic rheumatism, or cutaneous atopy, such as eczema or respiratory atopy or gingival hypertrophy;
4) for treating any dermal or epidermal proliferations whether benign or malignant, whether of viral origin or not, such as verruca vulgaris, verruca plana and epidermodysplasia verruciformis, oral or florid papillomatoses, T lymphoma, and proliferations which may be induced by ultraviolet radiation in particular in the case of baso- and spinocellular epitheliomas, and any precancerous skin lesions such as keratoacanthomas;
5) for treating other dermatological disorders such as immune dermatoses such as lupus erythematosus, bullous immune diseases and collagen diseases, such as scleroderma;
6) in the treatment of dermatological or general conditions with an immunological component;
7) in the treatment of skin disorders due to exposure to UV radiation and for repairing or combating skin aging, whether photoinduced or chronological or for reducing actinic keratoses and pigmentations, or any pathologies associated with chronologic or actinic aging, such as xerosis;
8) for combating sebaceous function disorders such as acne hyperseborrhoear or simple seborrhoea;
9) for preventing or treating cicatrization disorders, or for preventing or repairing stretch marks;
10) in the treatment of pigmentation disorders, such as hyperpigmentation, melasma, hypopigmentation or vitiligo;
11) in the treatment of lipid metabolism conditions, such as obesity, hyperlipidaemia or non-insulin-dependent diabetes;
12) in the treatment of inflammatory conditions such as arthritis;
13) in the treatment or prevention of cancerous or precancerous states;
14) in the prevention or treatment of alopecia of different origins, in particular alopecia due to chemotherapy or to radiation;
15) in the treatment of immune system disorders, such as asthma, diabetes mellitus type I, multiple sclerosis, or other selective dysfunctions of the immune system; and
16) in the treatment of conditions of the cardiovascular system such as arterosclerosis or hypertension.

The subject of the present invention is also a pharmaceutical composition comprising, in a physiologically acceptable medium, at least one compound of formula (I) as defined above.

The subject of the present invention is also the use of the compounds of formula (I) for manufacturing a composition intended for the treatment of the abovementioned conditions, in particular for regulating and/or restoring skin lipid metabolism.

The administration of the composition according to the invention may be carried out enterally, parenterally, topically or ocularly. Preferably, the pharmaceutical composition is packaged in a form suitable for application by the topical route.

By the enteral route, the composition may be provided in the form of tablets, gelatin capsules, sugar-coated tablets, syrups, suspensions, solutions, powders, granules, emulsions, suspensions of lipid or polymeric microspheres or nanospheres or vesicles allowing controlled release. By the parenteral route, the composition may be provided in the form of solutions or suspensions for perfusion or injection.

Compounds according to the invention are generally administered at a daily dose of about 0.001 mg/kg to 100 mg/kg of body weight, in 1 to 3 doses.

The compositions are used by the systemic route at a concentration generally of between 0.001% and 10% by weight, preferably between 0.01% and 1% by weight, relative to the weight of the composition.

By the topical route, the pharmaceutical composition according to the invention is more particularly intended for the treatment of the skin and the mucous membranes and may be provided in the form of salves, creams, milks, ointments, powders, impregnated pads, solutions, gels, sprays, lotions or suspensions. It may also be provided in the form of suspensions of lipid or polymeric microspheres or nanospheres or vesicles or of polymeric patches and of hydrogels allowing controlled release. This composition for the topical route may be provided in anhydrous form, in aqueous form or in the form of an emulsion.

The compounds are used by the topical route at a concentration which is generally between 0.001% and 10% by weight, preferably between 0.01% and 1% by weight, relative to the total weight of the composition.

The compounds of formula (I) according to the invention also find application in the cosmetic field, and more particularly for regulating and/or restoring skin lipid metabolism, in particular for preventing and/or treating the cutaneous signs of aging and/or of dry skin.

The subject of the invention is therefore also a composition comprising, in a cosmetically acceptable carrier, at least one of the compounds of formula (I).

The subject of the invention is also the cosmetic use of the compounds of formula (I) for body or hair hygiene.

The cosmetic composition according to the invention containing, in a cosmetically acceptable carrier, at least one compound of formula (I) or one of its optical or geometric isomers or one of its salts, may be provided in particular in the form of a cream, a milk, a lotion, a gel, suspensions of lipid or polymeric microspheres or nanospheres or vesicles, a soap or a shampoo.

The concentration of compound of formula (I) in the cosmetic composition is preferably between 0.001% and 3% by weight, relative to the total weight of the composition.

The pharmaceutical and cosmetic compositions as described above may in addition contain inert additives, or even pharmacodynamically active additives as regards the pharmaceutical compositions, or combinations of these additives, and in particular:
wetting agents;
flavor enhancers;
preservatives such as esters of parahydroxybenzoic acid;
stabilizers;
moisture regulators;
pH regulators;
osmotic pressure modifiers;
emulsifiers;
UV-A and UV-B screening agents;
antioxidants, such as α-tocopherol, butylated hydroxyanisole or butylated hydroxytoluene, Super Oxide Dismutase, Ubiquinol or certain metal chelators;
depigmenting agents such as hydroquinone, azelaic acid, caffeic acid or kojic acid;
emollients;
moisturizing agents such as glycerol, PEG 400, thiamorpholinone, and its derivatives, or urea;
antiseborrhoeic or anti-acne agents, such as S-carboxymethylcysteine, S-benzylcysteamine, their salts or their derivatives, or benzoyl peroxide;
antibiotics such as erythromycin and its esters, neomycin, clindamycin and its esters, tetracyclines;
antifungal agents such as ketoconazole or 4,5-polymethylene-3-isothiazolidones;
agents promoting hair regrowth, such as Minoxidil (2,4-diamino-6-piperidinopyrimidine 3-oxide) and its derivatives, Diazoxide (7-chloro-3-methyl-1,2,4-benzothiadiazine 1,1-dioxide) and Phenytoin (5,4-diphenylimidazolidine 2,4-dione);
nonsteroidal anti-inflammatory agents;
carotenoids and, in particular, β-carotene;
antipsoriatic agents such as anthralin and its derivatives;
5,8,11,14-eicosatetraynoic and 5,8,11-eicosatriynoic acids, their esters and amides;
retinoids, that is to say ligands for the RAR or RXR receptors, which may be natural or synthetic;
corticosteroids or oestrogens;
α-hydroxy acids and α-keto acids or their derivatives, such as lactic, malic, citric, glycolic, mandelic, tartaric, glyceric and ascorbic acids, and their salts, amides or esters, or β-hydroxy acids or their derivatives, such as salicylic acid and its salts, amides or esters;
ion channel, such as potassium channel, blockers;
or alternatively, more particularly for pharmaceutical compositions, in combination with medicaments known to interfere with the immune system (for example cyclosporine, FK 506, glucocorticoids, monoclonal antibodies, cytokines or growth factors, and the like).

Of course, persons skilled in the art will be careful to choose the possible compound(s) to be added to these compositions such that the advantageous properties intrinsically attached to the present invention are not or not substantially impaired by the addition envisaged.

Several examples of production of active compounds of formula (I) according to the invention, results of biological activity and various concrete formulations based on such compounds, will now be given by way of illustration and without being limiting in any manner.

EXAMPLE 1 methyl 7-{[4'-(2,4dioxothiazolidin-5-ylmethyl)biphenyl-3-ylmethyl]methylcarbamoyl}heptanoate (a) tert-butyl (3-bromobenzyl)carbamate 40.7 g (183 mmol) of 3-bromobenzylamine hydrochloride, 26 ml of triethylamine (183 mmol) and 450 ml of dichloromethane are introduced into a round-bottomed flask and under a nitrogen stream. 40 g (183 mmol) of di-tert-butyl dicarbonate are added in small quantities at room temperature and the mixture is stirred overnight. The reaction medium is poured into ice-cold water, extracted with dichloromethane, the organic phase decanted off, dried over magnesium sulphate and evaporated off. 46 g (88%) of the expected product are recovered.

(b) tert-butyl (3-bromobenyl)-N-methylcarbamate 128 g (447 mmol) of tert-butyl (3-bromobenzyl)carbamate and 800 ml of DMF are introduced into a round-bottomed flask and under a nitrogen stream. 19 g (475 mmol) of sodium hydride (60% in oil) are added in small quantities and the mixture is stirred until the gas emission ceases. 29.3 ml (470 mmol) of methyl iodide are then added and the mixture is stirred overnight. The reaction medium is poured into ice-cold water, extracted with ethyl acetate, the organic phase decanted off, dried over magnesium sulphate and evaporated off. 152.5 g (92%) of the expected product are recovered.

(c) tert-butyl (4'-formylbiphenyl-3-ylmethyl)methylcarbamate 61.5 g (205 mmol) of tert-butyl (3-bromobenzyl)-N-methylcarbamate, 40 g (260 mmol) of 4-formylbenzeneboronic acid and 800 ml of toluene are introduced into a three-necked flask and under argon. 205 ml of an aqueous potassium carbonate solution (2 M) are added dropwise, the reaction medium is degassed with argon and 7 g of tetrakis (triphenylphosphine)-palladium(0) chloride are added and the mixture is heated at 90° C. for 24 hours. The reaction medium is poured into water, extracted with dichloromethane, the organic phase decanted off, dried over magnesium sulphate and evaporated off. The residue obtained is purified by chromatography on a silica column eluted with a heptane and ethyl acetate (70–30) mixture. After evaporation of the solvents, 38 g (57%) of the expected product are recovered.

(d) tert-butyl [4'-(2,4-dioxothiazolidin-5-ylidenemethyl)biphenyl-3-ylmethyl]methylcarbamate 75.4 g (232 mmol) of tert-butyl (4'-formylbiphenyl-3-ylmethyl)methylcarbamate, 32.5 g (278 mmol) of 2,4-thiazolidinedione, 7.3 g (50 mmol) of piperidine acetate and 11 of toluene are introduced into a round-bottomed flask and under a nitrogen stream. The mixture is heated under reflux for five hours and the water formed is separated with the aid of a Dean-Stark. The reaction medium is cooled, and the precipitate formed is filtered off. 84 g (86%) of the expected product are recovered.

(e) tert-butyl [4'-(2,4-dioxothiazolidin-5-ylmethyl)biphenyl-3-ylmethyl]methylcarbamate 30 g (70.7 mmol) of tert-butyl [4'-(2,4-dioxothiazolidin-5-ylidenemethyl)biphenyl-3-ylmethyl]methylcarbamate in 500 ml of dioxane are introduced into a three-necked flask. The reaction medium is degassed, 30 g of palladium on carbon (10%) are added and the mixture is hydrogenated at a pressure of 3 bar at 60° C. The reaction medium is filtered, evaporated off and the residue obtained is purified by chromatography on a silica column eluted with a dichloromethane and methanol (99–1) mixture. 18 g (60%) of the expected product are recovered after evaporation of the solvents.

(f) 5-(3'-methylaminomethylbiphenyl-4-ylmethyl)thiazolidine-2,4-dione 18 g (42 mmol) of tert-butyl [4'-(2,4-dioxothiazolidin-5-ylmethyl)biphenyl-3-ylmethyl]methylcarbamate in 250 ml of dichloromethane are introduced into a round-bottomed flask and under a nitrogen stream, and 16 ml (208 mmol) of trifluoroacetic acid are added. The mixture is stirred at room temperature overnight and the reaction medium is hydrolysed with a saturated potassium carbonate solution. The mixture is extracted with dichloromethane, the organic phase decanted off, washed with water, dried over magnesium sulphate and evaporated off. The residue obtained is triturated in ethyl acetate and 14.4 g (78%) of the expected product are obtained.

(g) methyl 7-{[4'-(2,4-dioxothiazolidin-5-ylmethyl)biphenyl-3-ylmethyl]methylcarbamoyl}heptanoate 600 mg (1.36 mmol) of 5-(3'-methylaminomethylbiphenyl-4-ylmethyl)thiazolidine-2,4-dione, 10 ml of THF and 600 µl (4.3 mmol) of triethylamine are introduced into a round-bottomed flask and under a nitrogen stream. 220 µl (1.55 mmol) of methyl 8-chloro-8-oxooctanoate are added dropwise and the mixture is stirred for one hour. The reaction medium is poured into water, extracted with dichloromethane, the organic phase decanted off, washed with water, dried over magnesium sulphate and evaporated off. The residue obtained is purified by chromatography on a silica column eluted with a dichloromethane and ethyl acetate (80–20) mixture. After evaporation of the solvents, 350 mg (50%) of methyl 7-{[4'-(2,4-dioxothiazolidin-5-ylmethyl)biphenyl-3-ylmethyl]methylcarbamoyl}heptanoate are recovered in the form of an oil.

$^1$H NMR (CDCl$_3$): 0.88–1.40 (m, 4H); 1.62–1.70 (m, 4H); 2.31 (t, J=7.4 Hz, 2H); 2.40 (t, J=7.3 Hz, 2H); 2.96–2.99 (m, 3H); 3.15 (m, 1H); 3.58 (m, 1H); 3.66 (s, 3H); 4.57 (m, 1H); 4.60–4.66 (m, 2H); 7.23–7.55 (m, 8H); 9.15 (m, 1H).

EXAMPLE 2 methyl 9-{[4'-(2,4dioxothiazolidin-5-ylmethyl)biphenyl-3-ylmethyl]methylcarbamoyl}nonanoate In a manner similar to Example 1(g), by reacting 600 mg (1.36 mmol) of 5-(3'-methylaminomethylbiphenyl-4-ylmethyl)thiazolidine-2,4-dione obtained in 1(f) with 340 µl (1.52 mmol) of methyl 10-chloro-10-oxodecanoate, 500 mg (70%) of methyl 9-{[4'-(2,4-dioxothiazolidin-5-ylmethyl)biphenyl-3-ylmethyl]methylcarbamoyl}nonanoate are obtained in the form of an oil after purification by chromatography on a silica column eluted with a dichloromethane and ethyl acetate (80/20) mixture.

$^1$H NMR (CDCl$_3$): 1.26–1.32 (m, 8H); 1.59–1.65 (m, 4H); 2.20–2.43 (m, 4H); 2.95–2.99 (m, 3H); 3.16 (m, 1H); 3.55 (m, 1H); 3.85 (s, 3H); 4.54 (m, 1H); 4.60–4.65 (m, 2H); 7.19–7.54 (m, 8H); 9.75 (m, 1H).

EXAMPLE 3 methyl N-[4'-(2,4-dioxothiazolidin-5-ylmethyl)biphenyl-3-ylmethyl]-N-methylterephthalamate In a manner similar to Example 1(g), by reacting 600 mg (1.36 mmol) of 5-(3'-methylaminomethylbiphenyl-4-ylmethyl)thiazolidine-2,4-dione obtained in 1(f) with 310 mg (1.54 mmol) of methyl 4-chlorocarbonylbenzoate, 370 mg (60%) of methyl N-[4'-(2,4-dioxothiazolidin-5-ylmethyl)biphenyl-3-ylmethyl]-N-methylterephthalamate are obtained in the form of a white solid having a melting point of 186° C. after purification by chromatography on a silica column eluted with a dichloromethane and ethyl acetate (90/10) mixture.

EXAMPLE 4

3-cyclopentyl-N-[4'-(2,4-dioxothiazolidin-5-ylmethyl)biphenyl-3-ylmethyl]-N-methylpropionamide In a manner similar to Example 1(g), by reacting 500 mg (1.13 mmol) of 5-(3'-methylaminomethylbiphenyl-4-ylmethyl)thiazolidine-2,4-dione obtained in 1(f) with 200 mg (1.30 mmol) of 3-cyclopentylpropionyl chloride, 170 mg (25%) of 3-cyclopentyl-N-[4'-(2,4-dioxothiazolidin-5-ylmethyl)biphenyl-3-ylmethyl]-N-methylpropionamide are obtained in the form of a solid after purification by chromatography on a silica column eluted with a dichloromethane and methanol (99/1) mixture.

$^1$H NMR (CDCl$_3$): 1.10–1.14 (m, 2H); 1.26 (t, J=7.1 Hz, 3H); 1.50–1.79 (m, 6H); 2.42 (t, J=7.6 Hz, 2H); 2.97 (m, 3H); 3.15 (m, 1H); 3.58 (m, 1H); 4.52 (m, 1H); 4.61–4.66 (m, 2H); 7.20–7.55 (m, 8H); 9.48 (s, 1H).

EXAMPLE 5

N-[4'-(2,4-dioxothiazolidin-5-ylmethyl)biphenyl-3-ylmethyl]-N-methylnaphthalene-1-carboxamide In a manner similar to Example 1(g), by reacting 1 g (2.3 mmol) of 5-(3'-methylaminomethylbiphenyl-4-ylmethyl)thiazolidine-2,4-dione obtained in 1(f) with 380 µm (2.5 mmol) of 1-naphthoyl chloride, 460 mg (41%) of N-[4'-(2,4-dioxothiazolidin-5-ylmethyl)biphenyl-3-ylmethyl]-N-methylnaphthalene-1-carboxamide are obtained in the form of a white solid having a melting point of 120° C. after purification by chromatography on a silica column eluted with a heptane and ethyl acetate (80/20) mixture.

EXAMPLE 6

N-[4'-(2,4dioxothiazolidin-5-ylmethyl)biphenyl-3-ylmethyl]-N-methylnaphthalene-2-carboxamide In a manner similar to Example 1(g), by reacting 1 g (2.3 mmol) of 5-(3'-methylaminomethylbi-phenyl-4-ylmethyl)thiazolidine-2,4-dione obtained in 1(f) with 480 mg (2.5 mmol) of 2-naphthoyl chloride, 400 mg (40%) of N-[4'-(2,4-dioxothiazolidin-5-ylmethyl)biphenyl-3-ylmethyl]-N-methylnaphthalene-2-carboxamide are obtained in the form of a solid having a melting point of 218° C. after purification by chromatography on a silica column eluted with a heptane and ethyl acetate (70/30) mixture.

EXAMPLE 7

N-[4'-(2,4-dioxothiazolidin-5-ylmethyl)biphenyl-3-ylmethyl]-N-methyl-2-phenoxyacetamide In a manner similar to Example 1(g), by reacting 500 mg (1.53 mmol) of 5-(3'-methylamino-methylbiphenyl-4-ylmethyl)thiazolidine-2,4-dione obtained in 1(f) with 210 μl (1.52 mmol) of phenoxyacetyl chloride, 640 mg (91%) of N-[4'-(2,4-dioxothiazolidin-5-ylmethyl)biphenyl-3-ylmethyl]-N-methyl-2-phenoxyacetamide are obtained in the form of a white solid having a melting point of 140° C. after purification by chromatography on a silica column eluted with a heptane and ethyl acetate (60/40) mixture.

EXAMPLE 8

N-[4'-(2,4-dioxothiazolidin-5-ylmethyl)biphenyl-3-ylmethyl]-N-methyl-1-methyl-1H-pyrrole-2-carboxamide (a) 1-Methyl-1H-pyrrole-2-carboxylic acid chloride 500 mg (4 mmol) of 1-methyl-2-pyrrolecarboxylic acid in 5 ml of dichloromethane are introduced into a round-bottomed flask and under a nitrogen stream. There are added, dropwise, 790 μl (4 mmol) of dicyclohexylamine and, 30 minutes later, 290 μl (4 mmol) of thionyl chloride. The medium is stirred for 1 hour at room temperature and then heated for 2 hours at 50° C. The mixture is then diluted with ether and the precipitate is filtered off. The filtrate is evaporated off and a brown oil is obtained.

(b) N-[4'-(2,4dioxothiazolidin-5-ylmethyl)biphenyl-3-ylmethyl]-N-methyl-1-methyl-1H-pyrrole-2-carboxamide In a manner similar to Example 1(g), by reacting 500 mg (1.53 mmol) of 5-(3'-methylaminomethylbiphenyl-4-ylmethyl)thiazolidine-2,4-dione obtained in 1(f) with 220 mg (1.53 mmol) of 1-methyl-1H-pyrrole-2-carboxylic acid chloride, 316 mg (47%) of N-[4'-(2,4-dioxothiazolidin-5-ylmethyl)biphenyl-3-ylmethyl]-N-methyl-1-methyl-1H-pyrrole-2-carboxamide are obtained in the form of a white solid having a melting point of 184° C. after purification by chromatography on a silica column eluted with a heptane and ethyl acetate (60/40) mixture.

EXAMPLE 9

N-[4'-(2,4dioxothiazolidin-5-ylmethyl)biphenyl-3-ylmethyl]-N-methyladamantane-1-carboxamide In a manner similar to Example 1(g), by reacting 500 mg (1.53 mmol) of 5-(3'-methylaminomethylbiphenyl-4-ylmethyl)thiazolidine-2,4-dione obtained in 1(f) with 310 mg (1.56 mmol) of adamantane-1-carboxylic acid chloride, 390 mg of N-[4'-(2,4-dioxothiazolidin-5-ylmethyl)biphenyl-3-ylmethyl]-N-methyladamantane-1-carboxamide are obtained in the form of a white powder having a melting point of 77° C. after purification by chromatography on a silica column eluted with a heptane and ethyl acetate (70/30) mixture.

EXAMPLE 10

N-[4'-(2,4dioxothiazolidin-5-ylmethyl)biphenyl-3-ylmethyl]-N-methylbiphenyl-4-carboxamide In a manner similar to Example 1(g), by reacting 500 mg (1.53 mmol) of 5-(3'-methylaminomethylbiphenyl-4-ylmethyl)thiazolidine-2,4-dione obtained in 1(f) with 330 mg (1.52 mmol) of 4-biphenylcarboxylic acid chloride, 681 mg (88%) of N-[4'-(2,4-dioxothiazolidin-5-ylmethyl)biphenyl-3-ylmethyl]-N-methylbiphenyl-4-carboxamide are obtained in the form of a white powder having a melting point of 204° C. after trituration in ether.

EXAMPLE 11

N-[4'-(2,4-dioxothiazolidin-5-ylmethyl)biphenyl-3-ylmethyl]-N-methylbenzo[b]thio-phene-2-carboxamide In a manner similar to Example 1(g), by reacting 500 mg (1.53 mmol) of 5-(3'-methylaminomethylbiphenyl-4-ylmethyl)thiazolidine-2,4-dione obtained in 1(f) with 300 mg (1.52 mmol) of benzo[b]thiophene-2-carboxylic acid chloride, 509 mg (68%) of N-[4'-(2,4-dioxothiazolidin-5-ylmethyl)biphenyl-3-ylmethyl]-N-methylbenzo[b]thio-phene-2-carboxamide are obtained in the form of a white powder having a melting point of 187° C. after trituration in dichloromethane.

EXAMPLE 12

N-[4'-(2,4-dioxothiazolidin-5-ylmethyl)biphenyl-3-ylmethyl]-N-methyl-6-oxo-6-phenylhexanamide 320 mg (1.55 mmol) of 5-benzoylpentanoic acid in 5 ml of dichloromethane are introduced into a round-bottomed flask and under a nitrogen stream. 230 mg (1.7 mmol) of 1-hydroxybenzotriazole hydrate, 230 μl (1.7 mmol) of triethylamine and 500 mg (1.53 mmol) of 5-(3'-methylaminomethylbiphenyl-4-ylmethyl)thiazolidine-2,4-dione obtained in 1(f) are added. Next, at 0° C., 320 mg (1.7 mmol) of 1-(3-dimethylaminopropyl)-3-ethylcarbodiimide hydrochloride are added. The medium is stirred for 3 hours at room temperature. It is diluted with dichloromethane and washed with a saturated aqueous sodium hydrogen carbonate solution. The organic phase is dried over magnesium sulphate, filtered and evaporated off. The residue is purified by chromatography on a silica column eluted with a heptane and ethyl acetate (50/50) mixture. 590 mg (75%) of N-[4'-(2,4-dioxothiazolidin-5-ylmethyl)biphenyl-3-ylmethyl]-N- methyl-6-oxo-6-phenylhexanamide are obtained in the form of a white powder having a melting point of 48° C.

EXAMPLE 13

4-dimethylamino-N-[4'-(2,4-dioxothiazolidin-5-ylmethyl)biphenyl-3-ylmethyl]-N-methylnaphthalene-1-carboxamide In a manner similar to Example 12, by reacting 500 mg (1.53 mmol) of 5-(3'-methylaminomethylbiphenyl-4-ylmethyl)thiazolidine-2,4-dione obtained in 1(f) with 330 mg (1.53 mmol) of 4-dimethylaminonaphthalene-1-carboxylic acid, 520 mg (65%) of 4-dimethylamino-N-[4'-(2,4-dioxothiazolidin-5-ylmethyl)biphenyl-3-ylmethyl]-N-methylnaphthalene-1-carboxamide are obtained in the form of a yellowish foam having a melting point of 67° C. after purification by chromatography on a silica column eluted with a heptane and ethyl acetate (50/50) mixture.

EXAMPLE 14

N-[4'-(2,4dioxothiazolidin-5-ylmethyl)biphenyl-3-ylnethyl]-4-methanesulphonyl-N-methylbenzamide In a manner similar to Example 12, by reacting 500 mg (1.53 mmol) of 5-(3'-methylaminomethylbiphenyl-4-ylmethyl)thiazolidine-2,4-dione obtained in 1(f) with 310 mg (1.55 mmol) of 4-(methylsulphonyl)benzoic acid, 540 mg (69%) of N-[4'-(2,4-dioxothiazolidin-5-ylmethyl)biphenyl-3-ylmethyl]-4-methanesulphonyl-N-methylbenzamide are obtained in the form of a white solid having a melting point of 172° C. after purification by chromatography on a silica column eluted with a dichloromethane and methanol (98/2) mixture.

EXAMPLE 15

N-[4'-(2,4-dioxothiazolidin-5-ylmethyl)biphenyl-3-ylmethyl]-N-methyl-4-(1-phenylmethanoyl)benzamide (a) 4(1-phenylmethanoyl)benzoyl chloride In a manner similar to Example 9(a), starting with 500 mg (2.2 mmol) of 4-benzoylbenzoic acid, 490 mg (91%) of the expected product are obtained in the form of a white solid.

(b) N-[4'(2,4-dioxothiazolidin-5-ylmethyl)biphenyl-3-ylmethyl]-N-methyl-4-(1-phenylmethanoyl)benzamide In a manner similar to Example 1(g), by reacting 500 mg (1.53 mmol) of 5-(3'-methylaminomethyl-biphenyl-4-ylmethyl)thiazolidine-2,4-dione obtained in 1(f) with 380 mg (1.55 mmol) of 4-(1-phenylmethanoyl)benzoyl chloride, 660 mg (81%) of N-[4'-(2,4-dioxothiazolidin-5-ylmethyl) biphenyl-3-ylmethyl]-N-methyl-4-(1-phenylmethanoyl) benzamide are obtained in the form of a white powder having a melting point of 94° C. after purification by chromatography on a silica column eluted with a heptane and ethyl acetate (50/50) mixture.

EXAMPLE 16

6-(2-methoxyethoxymethoxy)-N-[4'-(2,4-dioxothiazolidin-5-ylmethyl)biphenyl-3-ylmethyl]-N-methyl-napthalene-2-carboxamide (a) methyl 6-hydroxynaphthalene-2-carboxylate 15.7 g (83 mmol) of 6-hydroxy-2-naphthoic acid in 160 ml of methanol are introduced into a round-bottomed flask. 8 ml of concentrated sulphuric acid are added and the mixture is heated under reflux for 8 hours. At room temperature, a precipitate forms. It is filtered off, rinsed with ether and dried. 14.1 g (84%) of the expected product are obtained in the form of a beige powder.

(b) methyl 6-(2-methoxyethoxymethoxy)naphthalene-2-carboxylate 14 g (69 mmol) of methyl 6-hydroxynaph-thalene-2-carboxylate in 90 ml of dimethylformamide and 90 ml of tetrahydrofuran are introduced into a round-bottomed flask and under a nitrogen stream. 3.3 g (82 mmol) of sodium hydride at 60% are added in small portions. When the gas emission has ceased, 8.7 ml (76 mmol) of 2-methoxyethoxymethyl chloride are added and the reaction medium is stirred for 3 hours at room temperature. It is then poured into ice-cold water and extracted with ether. The organic phase is dried over magnesium sulphate, filtered and evaporated off. The residue obtained is purified by chromatography on a silica column eluted with a heptane and ethyl acetate (80/20) mixture and 17 g (85%) of the expected product are obtained in the form of a colorless oil.

(c) 6-(2-methoxyethoxymethoxy)naphthale-2-carboxylic acid 16.9 g (58 mmol) of methyl 6-(2-methoxyethoxymethoxy)naphthalene-2-carboxylate in 200 ml of tetrahydrofuran and 20 ml of methanol are introduced into a round-bottomed flask. 1 ml of water and 12.9 g (322 mmol) of sodium hydroxide pellets are added. The reaction medium is stirred for 4 hours at room temperature. 1N hydrochloric acid is slowly added in the cold state up to pH 2–3. The mixture is extracted with ethyl acetate. The organic phase is dried over magnesium sulphate, filtered and then evaporated off. The residue is triturated in heptane, filtered and dried. 14.9 g (92%) of the expected product are obtained in the form of a white powder having a melting point of 110° C.

(d) 6-(2-methoxyethoxymethoxy)-N-[4'-(2,4-dioxothiazolidin-5-ylmethyl)biphenyl-3-ylmethyl]-N-methylnaphthalene-2-carboxamide In a manner similar to Example 12, by reacting 1.5 g (4.6 mmol) of 5-(3'-methylaminomethylbiphenyl-4-ylmethyl) thiazolidine-2,4-dione obtained in 1(f) with 1.27 g (4.6 mmol) of 6-(2-methoxyethoxymethoxy)naphthalene-2-carboxylic acid, 1.97 g (62%) of 6-(2-methoxyethoxymethoxy)-N-[4'-(2,4-dioxothiazolidin-5-ylmethyl)biphenyl-3-ylmethyl]-N-methylnaphthalene-2-carboxamide are obtained in the form of a white powder having a melting point of 68° C. after purification by chromatography on a silica column eluted with a heptane and ethyl acetate (50/50) mixture.

EXAMPLE 17

6hydroxy-N-[4'-(2,4-dioxothiazolidin-5-ylmethyl)
biphenyl-3-ylmethyl]-N-methylnaphthalene-2-carboxamide 1.5 g (2.5 mmol) of 6-(2-methoxyethoxymethoxy)-N-[4'-(2,4-dioxothiazolidin-5-ylmethyl)biphenyl-3-ylmethyl]-N-methylnaphthalene-2-carboxamide (obtained in Example 16) in 10 ml of tetrahydrofuran and 10 ml of methanol are introduced into a round-bottomed flask. 500 µl of concentrated sulphuric acid are added and the medium is stirred for 2 hours at room temperature. Water is added and the mixture is extracted with ethyl acetate. The organic phase is dried over magnesium sulphate, filtered and then evaporated off. The residue is purified by chromatography on a silica column eluted with a heptane and ethyl acetate (30/70) mixture. 1.26 g (99%) of 6-hydroxy-N-[4'-(2,4-dioxothiazolidin-5-ylmethyl)biphenyl-3-ylmethyl]-N-methylnaphthalene-2-carboxamide are obtained in the form of a white powder having a melting point of 218° C.

EXAMPLE 18

N-[4'-(2,4-dioxothiazolidine-5-ylmethyl)biphenyl-3-ylmethyl]-N-methyl-4-methylsulphanylbenzamide (a) 4-methylsulphanylbenzoyl chloride In a manner similar to Example 9(a), starting with 400 mg (2.4 mmol) of 4-(methylthio)benzoic acid, 440 mg (99%) of the expected product are obtained in the form of a yellowish solid.

(b) N-[4'-(2,4-dioxothiazolidin-5-ylmethyl)biphenyl-3-methyl]-N-methyl-4-methylsulphanylbenzamide In a manner similar to Example 1(g), by reacting 500 mg (1.53 mmol) of 5-(3'-methylaminomethylbiphenyl-4-ylmethyl)thiazolidine-2,4-dione obtained in 1(f) with 290 mg (1.55 mmol) of 4-methylsulphanylbenzoyl chloride, 470 mg (64%) of N-[4'-(2,4-dioxothiazolidin-5-ylmethyl)biphenyl-3-ylmethyl]-N-methyl-4-methylsulphanylbenzamide are obtained in the form of a white powder having a melting point of 203–7° C. after recrystallization from methanol.

EXAMPLE 19

(S)-3-(3'-{[(1-biphenyl-4-ylmethanoyl)methylamino]methyl}biphenyl-4-yl)-2-ethoxypropionic acid (a) Ethoxyacetyl Chloride 25 g (240 mmol) of ethoxyacetic acid in 300 ml of dichloromethane are introduced into a round-bottomed flask and under a nitrogen stream. 47.6 ml (239 mmol) of dicyclohexylamine are added. The medium is stirred for 1 hour at room temperature. 19.2 ml (265 mmol) of thionyl chloride are added and the mixture is stirred for 3 hours. Ethyl ether is added to the reaction medium, the precipitate formed is filtered off and rinsed with ether. After evaporation of the filtrate, 29 g (100%) of the expected product are obtained in the form of a brown liquid.

(b) 3-(2-ethoxyethanoyl)-4benzyloxazolidin-2-one 36.7 g (207 mmol) of (S)4-benzyloxazolidin-2-one in 800 ml of THF are introduced into a round-bottomed flask and under a nitrogen stream. The reaction medium is cooled to −78° C. and 83 ml (207 mmol) of n-butyllithium (2.5 M/hexane) are added dropwise. 30 minutes later, 25.4 g (207 mmol) of ethoxyacetyl chloride are added at −78° C. The reaction medium is stirred for 24 hours and then poured into a saturated aqueous sodium chloride solution and extracted with ethyl acetate. The organic phase is dried over magnesium sulphate, filtered and evaporated off. 30.6 g (56%) of the expected product are obtained in the form of an orange-colored oil after purification by chromatography on a silica column eluted with a heptane and ethyl acetate (60/40) mixture.

(c) methyl (2S, 3R)-3-(3'-[(tert-butoxycarbonylmethylamino)methyl]biphenyl-4yl)-2-ethoxy-3-hydroxypropionate 21.9 g (83 mmol) of 3-(2-ethoxyethanol)4-benzyloxazolidin-2-one and 100 ml of dichloromethane are introduced into a round-bottomed flask and under argon. 103 ml (103 mmol) of dibutylborane trifluoromethanesulphonate and 18 ml (104 mmol) of 47 N-ethyldiisopropylamine are successively added, at 0° C., dropwise, and the mixture is stirred for one hour. At −78° C., a solution of 23.5 g (69 mmol) of tert-butyl (4'-formylbiphenyl-3-ylmethyl)methylcarbamate obtained in 1(c) in 100 ml of dichloromethane is added and the mixture is stirred overnight. It is treated with a buffer solution pH=7 (170 ml) in 500 ml of methanol and then with a solution of hydrogen peroxide (170 ml) in 500 ml of methanol and the mixture is stirred for 1 hour 30 minutes at 0° C. The reaction medium is poured into water, and extracted with dichloromethane. The organic phase is dried over magnesium sulphate, filtered and evaporated off. The residue obtained is purified by chromatography on a silica column eluted with a heptane and ethyl acetate (70/30) mixture and 21 g (51%) of the expected product are obtained.

(d) methyl (2S,3R)-2-ethoxy-3-hydroxy-3-(3'-methylaminomethylbiphenyl-4yl)propionate 21 g (47.3 mmol) of methyl (2S,3R)-3-{3'-[(tert-butoxycarbonylmethylamino)methyl]biphenyl-4-yl}-2-ethoxy-3-hydroxypropionate, 8.76 ml (54.9 mmol) of triethylsilane in 300 ml of trifluoroacetic acid are introduced into a round-bottomed flask and under a nitrogen stream. The reaction medium is stirred for 4 hours at room temperature. Ethyl acetate is then added and the mixture is neutralized with sodium hydroxide. The organic phase is washed with a saturated aqueous sodium chloride solution, dried over magnesium sulphate, filtered and evaporated off. 19.6 g (100%) of the expected crude product are obtained.

(e) methyl (S)-2-ethoxy-3-(3'-methylaminomethylbiphenyl-4-yl)propionate 19.6 g of the crude product methyl (2S,3R)-2-ethoxy-3-hydroxy-3-(3'-methylaminomethylbiphenyl-4-yl)propionate are dissolved in 200 ml of trifluoroacetic acid and 41.7 ml (297 mmol) of triethylamine are added. The reaction medium is stirred at room temperature for 48 hours and then extracted with ethyl acetate. The organic phase is decanted off, washed with a sodium hydroxide solution and then with a saturated aqueous sodium chloride solution, dried over magnesium sulphate, filtered and evaporated off. The residue obtained is purified by chromatography on a silica column eluted with a dichloromethane and methanol (95/5) mixture. 1.6 g (10%) of the expected product are obtained.

(f) methyl (S)-3-(3'-{[(1-biphenyl-4-ylmethanoyl)methylamino]methyl}biphenyl-4yl)-2-ethoxypropionate In a manner similar to Example 1(g), by reacting 500 mg (1.5 mmol) of methyl (S)-2-ethoxy-3-(3'-methylaminomethylbiphenyl-4-yl)propionate with 680 mg (3.1 mmol) of 4-biphenylcarboxylic acid chloride, 360 mg (47%) of the expected product are obtained after purification by chromatography on a silica column eluted with a heptane and ethyl acetate (70/30) mixture.

(g) (S)-3-(3'-{[(1-biphenyl-4-ylmethanoyl)methylamino]methyl}biphenyl-4yl)-2-ethoxypropionic acid 360 mg (0.7 mmol) of methyl (S)-3-(3'-{[(1-biphenyl-4-ylmethanoyl)methylamino]methyl}biphenyl-4-yl)-2-ethoxypropionate in 10 ml of THF are introduced into a round-bottomed flask. 60 mg (1.4 mmol) of lithium hydroxide monohydrate, 1 ml of water and 1 ml of methanol are added and the mixture is stirred for 4 hours. The reaction medium is poured into water, acidified to pH 1, extracted with ethyl acetate, the organic phase decanted off, dried over magnesium sulphate and evaporated off. The residue obtained is purified by chromatography on a silica column eluted with a heptane and ethyl acetate (50/50) mixture and 280 mg (80%) of (S)-3-(3'-{[(1-biphenyl-4-ylmethanoyl)methylamino]methyl}biphenyl-4-yl)-2-ethoxypropionic acid are obtained in the form of an amorphous white solid.

$^1$H NMR (CDCl$_3$): 1.19 (t, J=8 Hz, 3H); 2.96–3.09 (m, 3H); 3.05 (dd, J=14.1 Hz and J=7.8 Hz, 1H); 3.17 (dd, J=14.1 Hz and J=4 Hz, 1H); 3.45–3.61 (m, 2H); 4.12 (m, 1H); 4.64–4.84 (m, 2H); 7.25–7.56 (m, 17H).

EXAMPLE 20

(S)-2-ethoxy-3-(3'-{[(methyl(6-oxo-6-phenylhexanoyl)amino]methyl}biphenyl-4-yl)propionic acid (a) methyl (S)-2-ethoxy-3-(3'{([methyl(6-oxo-6-phenylhexanoyl)amino]methyl}biphenyl-4yl)propionate In a manner similar to Example 12, by reacting 660 mg (2 mmol) of methyl (S)-2-ethoxy-3-(3'-methylaminomethylbiphenyl-4-yl)propionate obtained in 19(e) with 346 mg (1.68 mmol) of 5-benzoylpentanoic acid, 330 mg (33%) of the expected product are obtained after purification by chromatography on a silica column eluted with a heptane and ethyl acetate (50/50) mixture.

(b) (S)-2-ethoxy-3-(3'-{[methyl(6-oxo-6-phenylhexanoyl)amino]methyl}biphenyl-4yl)propionic acid In a manner similar to Example 19(g), starting with 330 mg (0.64 mmol) of methyl (S)-2-ethoxy-3-(3'-{[methyl(6-oxo-6-phenylhexanoyl)amino]methyl}biphenyl-4-yl)propionate, 230 mg (72%) of (S)-2-ethoxy-3-(3'-{[methyl(6-oxo-6-phenylhexanoyl)amino]methyl}biphenyl-4-yl)propionic acid are obtained in the form of a yellow oil after purification by chromatography on a silica column.

$^1$H NMR (CDCl$_3$): 1.20 (m, 3H); 1.77–1.85 (m, 4H); 2.44 (m, 2H); 2.95–2.98 (m, 3H); 3.01 (m, 2H); 3.05 (m, 1H); 51 3.15 (m, 1H); 3.46–3.61 (m, 2H); 4.10 (2s, 1H); 4.59–4.64 (m, 2H); 7.18–7.55 (m, 11H); 7.90–7.96 (m, 2H).

EXAMPLE 21

1-[4'-(2,4-dioxothiazolidin-5-ylmethyl)biphenyl-3-yl]-1-methyl-3-naphthalen-2-ylurea (a) (3-bromophenyl)methylamine 10 g (58 mmol) of 3-bromoaniline and 34 ml (204 mmol) of triethylorthoformate are introduced into a round-bottomed flask and under a nitrogen stream. The reaction medium is heated under reflux for 7 hours. The triethylorthoformate is then evaporated off. The residue is dissolved in ethanol and 4.9 g (12.8 mmol) of sodium borohydride are added at 0° C. The medium is stirred overnight at room temperature. It is then poured into water and extracted with ethyl acetate. The organic phase is washed with a saturated aqueous sodium chloride solution, dried over magnesium sulphate, filtered and then evaporated off. The residue obtained is purified by chromatography on a silica column eluted with a heptane and ethyl acetate (90/10) mixture and 5 g (46%) of the expected product are obtained in the form of a light oil.

(b) 3'-methylaminobiphenyl-4carbaldehyde

In a manner similar to Example 1(c), by reacting 4.3 g (23.2 mmol) of (3-bromophenyl)methylamine with 5.2 g (34.8 mmol) of 4-formylbenzeneboronic acid, 2.9 g (59%) of the expected product are obtained in the form of a yellow solid after purification by chromatography on a silica column eluted with a heptane and ethyl acetate (90/10) mixture.

(c) 5-(3'-methylaminobiphenyl-4-ylmethylene)thiazolidine-2,4-dione

In a manner similar to Example 1(d), by reacting 2.9 g (13.7 mmol) of 3'-methylaminobiphenyl-4-carbaldehyde with 1.6 g (13.7 mmol) of 2,4-thiazolidinedione, 3.9 g (91%) of the expected product are obtained after trituration in dichloromethane and ether.

(d) 1-[4'(2,4-dioxothiazolidin-5-ylidenemethyl)biphenyl-3-yl]-1-methyl-3-naphthalen-2-ylurea 500 mg (1.6 mmol) of 5-(3'-methylaminobiphenyl-4-ylmethylene)thiazolidine-2,4-dione in 10 ml of dichloromethane and 540 mg (3.2 mmol) of naphthyl isocyanate are introduced into a round-bottomed flask and under a nitrogen stream. The mixture is stirred at 35° C. for 4 hours. The reaction medium is filtered and the solid is rinsed with dichloromethane. The filtrate is evaporated off and 660 mg (86%) of the expected product are obtained in the form of a yellow powder.

(e) 1-[4'(2,4-dioxothiazolidin-5-ylmethyl)biphenyl-3-yl]-1-methyl-3-naphthalen-2-ylurea In a manner similar to Example 1(e), starting with 660 mg (1.38 mmol) of 1-[4'-(2,4-dioxothiazolidin-5-ylidenemethyl)biphenyl-3-yl]- 1-methyl-3-naphthalen-2-ylurea, 320 mg (48%) of 1-[4'-(2,4-dioxothiazolidin-5-ylmethyl)biphenyl-3-yl]-1-methyl-3-naphthalen-2-ylurea are obtained in the form of a white powder having a melting point of 196° C. after purification by chromatography on a silica column eluted with a heptane and ethyl acetate (70/30) mixture.

EXAMPLE 22

3-(4-dinethylaminophenyl)-1-[4'-(2,4-dioxothiazolidin-5-ylmethyl)biphenyl-3-yl]-1-methylurea (a) 3-(4-dimethylaminophenyl)-1-[4'-(2,4-dioxothiazolidin-5-ylidenemethyl)biphenyl-3-yl]-1-methylurea In a manner similar to Example 22(d), by reacting 500 mg (1.6 mmol) of 5-(3'-methylaminobiphenyl-4-ylmethylene)thiazolidine-2,4-dione obtained in 21(c) with 520 mg (3.2 mmol) of 4-(dimethylamino)phenyl isocyanate, 760 mg (100%) of the expected product are obtained in the form of a yellow powder.

(b) 3-(4-dimethylaminophenyl)-1-[4'-(2,4-dioxothiazolidin-5-ylmethyl)biphenyl-3-yl]-1-methylurea In a manner similar to Example 1(e), starting with 760 mg (1.6 mmol) of 3-(4-dimethylaminophenyl)-1-[4'-(2,4-dioxothiazolidin-5-ylidenemethyl)biphenyl-3-yl]-1-methylurea, 330 mg (43%) of 3-(4-dimethylaminophenyl)-1-[4'-(2,4-dioxothiazolidin-5-ylmethyl)biphenyl-3-yl]-1-methylurea are obtained in the form of a white powder having a melting point of 102° C. after purification by chromatography on a silica column eluted with a heptane and ethyl acetate (60/40) mixture.

EXAMPLE 23

(S)-2-ethoxy-3-{3'-[({1-[6-(2-methoxy-ethoxymethoxy)naphthalen-2-yl]methanoyl}methylamino)methyl]biphenyl-4-yl}propionic acid (a) (S)-2-ethoxy-3-{3'-[({1-[6-(2-methoxy-ethoxymethoxy)naphthalen-2-yl]methanoyl}methylamino)methyl]biphenyl-4-yl}propionic acid In a manner similar to Example 13, by reacting 380 mg (1.16 mmol) of methyl (S)-2-ethoxy-3-(3'-methylaminomethylbiphenyl-4-yl)propionate obtained in 19(e) with 350 mg (1.27 mmol) of 6-(2-methoxy-ethoxymethoxy) naphthalene-2-carboxylic acid (prepared in 16(c)), 110 mg (16%) of the expected product are obtained after purification by chromatography on a silica column eluted with a heptane and ethyl acetate (50/50) mixture.

(b) (S)-2-ethoxy-3-{3'-[({1-[6-(2-methoxy-ethoxymethoxy)naphthalen-2-yl]methanoyl}-methylamino)methyl]biphenyl-4-yl}propionic acid In a manner similar to Example 19(g), by reacting 110 mg (0.18 mmol) of methyl (S)-2-ethoxy-3-{3'-[({1-[6-(2-methoxyethoxymethoxy)naphthalen-2-yl]methanoyl}methylamino)methyl]biphenyl-4-yl}propionate with 16 mg (0.38 mmol) of lithium hydroxide monohydrate, 30 mg (42%) of (S)-2-ethoxy-3-{3'-[({1-[6-(2-methoxy-ethoxymethoxy)naphthalen-2-yl]methanoyl}methylamino)methyl]biphenyl-4-yl}propionic acid are obtained in the form of a yellow oil after purification by chromatography on a silica column eluted with a heptane and ethyl acetate (50/50) mixture then with pure ethyl acetate.

$^1$H NMR (CDCl$_3$): 1.18 (t, J=6.9 Hz, 3H); 2.90–3.17 (m, 5H); 3.37 (s, 3H); 3.44–3.64 (m, 4H); 3.86 (m, 2H); 4.11 (m, 1H); 4.70 (m, 2H); 5.39 (s, 2H); 7.23–7.54 (m, 11H); 7.75 (m, 2H); 7.91 (s, 1H).

EXAMPLE 24

6-(methoxymethoxy)-N-[4'-(2,4-dioxothiazolidin-5-ylmethyl)biphenyl-3-ylmethyl]-N-methylnaphthalene-2-carboxamide In a manner similar to Example 12, by reacting 500 mg (1.53 mmol) of 5-(3'-methylamino-methylbiphenyl-4-ylmethyl)thiazolidine-2,4-dione obtained in 1(f) with 371 mg (1.6 mmol) of 6-methoxymethoxynaphthalene-2-carboxylic acid, 648 mg (75%) of 6-(methoxymethoxy)-N-[4'-(2,4-dioxothiazolidin-5-ylmethyl)biphenyl-3-ylmethyl]-N-methylnaphthalene-2-carboxamide are obtained in the form of a white powder having a melting point of 160° C. after purification by chromatography on a silica column eluted with a heptane and ethyl acetate (50/50) mixture.

$^1$H NMR (DMSO d6; 400 MHz): 2.96 (broad s, 3H); 3.19 (dd, J=9.2 Hz and J=14.1 Hz, 1H); 3.41 (s, 3H); 3.44 (dd, J=4.2 Hz and J=14.1 Hz, 1H); 4.58–4.82 (m, 2H); 4.97 (dd, J=4.3 Hz and J=9.1 Hz, 1H); 7.25–8.03 (m, 14H); 12.10 (broad s, 1H)

EXAMPLE 25

6-(methoxycarbonyl)-N-[4'-(2,4-dioxothiazolidin-5-ylmethyl)biphenyl-3-ylmethyl]-N-methylnaphthalene-2-carboxamide In a manner similar to Example 12, by reacting 500 mg (1.53 mmol) of 5-(3'-methylamino-methylbiphenyl-4-ylmethyl)thiazolidine-2,4-dione obtained in 1(f) with 370 mg (1.6 mmol) of 6-methoxycarbonylnaphthalene-2-carboxylic acid, 580 mg (67%) of 6-(methoxycarbonyl)-N-[4'-(2,4-dioxothiazolidin-5-ylmethyl)biphenyl-3-ylmethyl]-N-methylnaphthalene-2-carboxamide are obtained in the form of a white powder having a melting point of 125–127° C. after purification by chromatography on a silica column eluted with a heptane and ethyl acetate (50/50) mixture.

$^1$H NMR (DMSO d6; 400 MHz): 2.92–3.01 (m, 3H); 3.18 (m, 1H); 3.44 (m, 1H); 3.93 (s, 3H); 4.59–4.80 (m, 2H); 4.97 (m, 1H); 7.20–7.70 (m, 9H); 8.00–8.20 (m, 3H); 8.23 (m, 1H); 8.69 (m, 1H); 12.10 (broad s, 1H).

EXAMPLE 26

6-(propyloxy)-N-[4'-(2,4-dioxothiazolidin-5-ylmethyl)biphenyl-3-ylmethyl]-N-methylnaphthalene-2-carboxamide In a manner similar to Example 12, by reacting 500 mg (1.53 mmol) of 5-(3'-methylamino-methylbiphenyl-4-ylmethyl)thiazolidine-2,4-dione obtained in 1(f) with 370 mg (1.6 mmol) of 6-propyloxynaphthalene-2-carboxylic acid, 530 mg (61%) of 6-(propyloxy)-N-[4'-(2,4-dioxothiazolidin-5-ylmethyl)biphenyl-3-ylmethyl]-N-methylnaphthalene-2-carboxamide are obtained in the form of a white powder having a melting point of 108–110° C. after purification by chromatography on a silica column eluted with a heptane and ethyl acetate (50/50) mixture.

$^1$H NMR (DMSO d6; 400 MHz): 1.00 (t, J=7.4 Hz, 3H); 1.80 (m, 2H); 2.96 (broad s, 3H); 3.17 (dd, J=9.2 Hz and J=14.1 Hz, 1H); 3.44 (dd, J=4.2 Hz and J=14.1 Hz, 1H); 4.06 (t, J=6.5 Hz, 2H); 4.63–4.77 (m, 2H); 4.96 (dd, J=4.3 Hz and J=9.1 Hz, 1H); 7.19–7.98 (m, 14H); 12.10 (broad s, 1H).

EXAMPLE 27

6-(hexyloxy)-N-[4'-(2,4-dioxothiazolidin-5-ylmethyl)biphenyl-3-ylmethyl]-N-methylnaphthalene-2-carboxamide In a manner similar to Example 12, by reacting 500 mg (1.53 mmol) of 5-(3'-methylamino-methylbiphenyl-4-ylmethyl)thiazolidine-2,4-dione obtained in 1(f) with 436 mg (1.6 mmol) of 6-hexyloxynaphthalene-2-carboxylic acid, 520 mg (56%) of 6-(hexyloxy)-N-[4'-(2,4-dioxothiazolidin-5-ylmethyl)biphenyl-3-ylmethyl]-N-methylnaphthalene-2-carboxamide are obtained in the form of a white powder having a melting point of 117° C. after purification by chromatography on a silica column eluted with a heptane and ethyl acetate (60/40) mixture.

$^1$H NMR (DMSO d6; 400 MHz): 0.88 (m, 3H); 1.32 (m, 4H); 1.44 (m, 2H); 1.79 (m, 2H); 2.96 (broad s, 3H); 3.17 (dd, J=9.2 Hz and J=14.1 Hz, 1H); 3.44 (dd, J=4.2 Hz and J=14.1 Hz, 1H); 4.09 (t, J=6.5 Hz, 2H); 4.63–4.77 (m, 2H); 4.96 (dd, J=4.3 Hz and J=9.1 Hz, 1H); 7.19–7.98 (m, 14H); 12.10 (broad s, 1H).

EXAMPLE 28

6-(nonyloxy)-N-[4'-(2,4dioxothiazolidin-5-ylmethyl)biphenyl-3-ylmethyl]-N-methylnaphthalene-2-carboxamide In a manner similar to Example 12, by reacting 500 mg (1.53 mmol) of 5-(3'-methylamino-methylbiphenyl-4-ylmethyl)thiazolidine-2,4-dione obtained in 1(f) with 503 mg (1.6 mmol) of 6-nonyloxynaphthalene-2-carboxylic acid, 590 mg (59%) of 6-(nonyloxy)-N-[4'-(2,4-dioxothiazolidin-5-ylmethyl)biphenyl-3-ylmethyl]-N-methylnaphthalene-2-carboxamide are obtained in the form of a white powder having a melting point of 117° C. after purification by chromatography on a silica column eluted with a heptane and ethyl acetate (60/40) mixture.

$^1$H NMR (DMSO d6; 400 MHz): 0.85 (m, 3H); 1.20–1.40 (m, 10H); 1.45 (m, 2H); 1.78 (m, 2H); 2.96 (broad s, 3H); 3.17 (dd, J=9.2 Hz and J=14.1 Hz, 1H); 3.44 (dd, J=4.2 Hz and J=14.1 Hz, 1H); 4.09 (t, J=6.5 Hz, 2H); 4.63–4.77 (m, 2H); 4.96 (dd, J=4.3 Hz and J=9.1 Hz, 1H); 7.19–7.98 (m, 14H); 12.10 (broad s, 1H).

EXAMPLE 29

N-[4'-(2,4-dioxothiazolidin-5-ylmethyl)biphenyl-3-ylmethyl]-N-methyl-4'-propylbiphenyl-2-carboxamide In a manner similar to Example 12, by reacting 500 mg (1.53 mmol) of 5-(3'-methylamino-methylbiphenyl-4-ylmethyl)thiazolidine-2,4-dione obtained in 1(f) with 384 mg (1.6 mmol) of 4-(4'-propylphenyl)benzoic acid, 602 mg (68%) of N-[4'-(2,4-dioxothiazolidin-5-ylmethyl)biphenyl-3-ylmethyl]-N-methyl-4'-propylbiphenyl-2-carboxamide are obtained in the form of a white powder after purification by chromatography on a silica column eluted with a heptane and ethyl acetate (60/40) mixture.

$^1$H NMR (DMSO d6; 400 MHz): 0.91 (t, J=7.3 Hz, 3H); 1.72 (m, 2H); 2.58 (m, 2H); 2.93 (broad s, 3H); 3.19 (dd, J=9.2 Hz and J=14.1 Hz, 1H); 3.43 (dd, J=4.2 Hz and J=14.1 Hz, 1H); 4.58–4.78 (m, 2H); 4.96 (dd, J=4.3 Hz and J=9.1 Hz, 1H); 7.20–7.75 (m, 16H); 12.10 (broad s, 1H).

EXAMPLE 30

N-[4'-(2,4-dioxothiazolidin-5-ylmethyl)biphenyl-3-ylmethyl]-N-methyl-4-phenoxybenzamide In a manner similar to Example 12, by reacting 500 mg (1.53 mmol) of 5-(3'-methylamino-methylbiphenyl-4-ylmethyl)thiazolidine-2,4-dione obtained in 1(f) with 343 mg (1.6 mmol) of 4-phenoxybenzoic acid, 545 mg (68%) of N-[4'-(2,4-dioxothiazolidin-5-ylmethyl)biphenyl-3-ylmethyl]-N-methyl-4-phenoxybenzamide are obtained in the form of a white powder having a melting point of 95° C. after purification by chromatography on a silica column eluted with a heptane and ethyl acetate mixture in a polarity gradient from (80/20) to (60/40).

EXAMPLE 31

N-[4'-(2,4-dioxothiazolidin-5-ylmethyl)biphenyl-3-ylmethyl]-N-methyl-7-oxo-7-phenylheptanamide In a manner similar to Example 12, by reacting 500 mg (1.53 mmol) of 5-(3'-methylamino-methylbiphenyl-4-ylmethyl)thiazolidine-2,4-dione obtained in 1(f) with 352 mg (1.6 mmol) of 6-benzoylhexanoic acid, 610 mg (75%) of N-[4'-(2,4-dioxothiazolidin-5-ylmethyl)biphenyl-3-ylmethyl]-N-methyl-7-oxo-7-phenylheptanamide are obtained in the form of a white powder having a melting point of 55–56° C. after purification by chromatography on a silica column eluted with a heptane and ethyl acetate mixture in a polarity gradient from (70/30) to (50/50).

EXAMPLE 32

4'-(2-methoxyethoxymethoxy)-N-[4'-(2,4-dioxothiazolidin-5-ylmethyl)biphenyl-3-ylmethyl]-N-methylbiphenyl-4-carboxamide (a) methyl 4'(2-methoxyethoxymethoxy)biphenyl-4-carboxylate 10 g (43.8 mmol) of 4'-hydroxybiphenyl-4-carboxylic acid methyl ester, 100 ml of THF and 150 ml of DMF are introduced in order and under a nitrogen stream into a 500 ml three-necked flask. 1.93 g (48.2 mmol) of NaH at 60% in oil are added in small portions and the mixture is stirred at room temperature for 15 hours. 5.75 ml of 1-chloromethoxy-2-methoxyethane are added dropwise, and the mixture is stirred at room temperature for 30 minutes. The reaction medium is poured over a 1N HCl solution and extracted with ethyl acetate. The organic phase is washed with water and dried over magnesium sulphate. After filtration and evaporation 12 g of 4'-(2-methoxyethoxymethoxy)biphenyl-4-carboxylic acid methyl ester are obtained in the form of a beige powder after filtration and evaporation (yield=87%).

(b) 4'-(2-methoxyethoxymethoxy)biphenyl-4-carboxylic acid 10 g (31.6 mmol) of 4'-(2-methoxyethoxymethoxy)biphenyl-4-carboxylic acid methyl ester, 100 ml of methanol and 31 ml of a 10 M NaOH solution are introduced, in order, into a 250 ml three-necked flask. The mixture is stirred at 80° C. for 30 minutes. After returning to room temperature, the reaction medium is poured over water and acidified with a 1 N HCl solution. The precipitate is filtered off. It is taken up in heptane. After filtering and drying, 9 g of 4'-(2-methoxyethoxymethoxy)biphenyl-4-carboxylic acid are obtained in the form of a beige powder (yield=98%).

(c) 4'-(2-methoxyethoxymethoxy)-N-[4'-(2,4-dioxothiazolidin-5-ylmethyl)biphenyl-3-ylmethyl]-N-methylbiphenyl-4carboxanide In a manner similar to Example 12, by reacting 4 g (12.3 mmol) of 5-(3'-methylaminomethylbiphenyl-4-ylmethyl)thiazolidine-2,4-dione obtained in 1(f) with 3.58 g (12.3 mmol) of 4'-(2-methoxyethoxymethoxy)biphenyl-4-carboxylic acid, 2.9 g (38%) of 4'-(2-methoxyethoxymethoxy)-N-[4'-(2,4-dioxothiazolidin-5-ylmethyl)biphenyl-3-ylmethyl]-N-methylbiphenyl-4-carboxamide are obtained in the form of a white powder having a melting point of 126–128° C. after purification by chromatography on a silica column eluted with a heptane and ethyl acetate (50/50) mixture, followed by recrystallization from methanol.

$^1$H NMR (DMSO d6; 400 MHz): 2.93 (m, 3H); 3.15–3.22 (m, 4H); 3.41–3.47 (m, 3H); 3.72 (m, 2H); 4.614.75 (m, 2H); 4.96 (dd, J=4.3 Hz and J=9.1 Hz, 1H); 5.29 (broad s, 2H); 7.11–7.68 (m, 16H); 12.10 (broad s, 1H).

EXAMPLE 33

4'-hydroxy-N-[4'-(2,4-dioxothiazolidin-5-ylmethyl)biphenyl-3-ylmethyl]-N-methylbiphenyl-4-carboxamide 1.6 g of 4'-(2-methoxyethoxymethoxy)-N-[4'-(2,4-dioxothiazolidin-5-ylmethyl)biphenyl-3-ylmethyl]-N-methylbiphenyl-4-carboxamide, 100 ml of methanol and 1 ml of 98% sulphuric acid are introduced, in order, into a 250 ml three-necked flask. The mixture is stirred at room temperature for 18 hours. The reaction medium is concentrated. It is taken up in ethyl acetate and it is washed twice with water. The organic phase is dried over magnesium sulphate. After filtration and evaporation, the product obtained is recrystallized from an acetone/dichloromethane mixture. After filtration and drying, 1.34 g (99%) of 4'-hydroxy-N-[4'-(2,4-dioxothiazolidin-5-ylmethyl)biphenyl-3-ylmethyl]-N-methylbiphenyl-4-carboxamide are obtained in the form of a white powder having a melting point of 211–213° C.

$^1$H NMR (DMSO d6; 400 MHz): 2.93 (m, 3H); 3.18 (dd, J=9.6 Hz and J=14.1 Hz, 1H); 3.43 (dd, J=4.3 Hz and J=14.1 Hz, 1H); 4.61–4.75 (m, 2H); 4.96 (dd, J=4.3 Hz and J=9.6 Hz, 1H); 6.85–7.63 (m, 16H); 9.62 (broad s, 1H); 12.10 (broad s, 1H).

EXAMPLE 34

1-[4'-(2,4-dioxothiazolidin-5-ylmethyl)biphenyl-3-yl]-3-(4-hexyloxyphenyl)-1-methylurea

(a) tert-butyl (3-bromophenyl)carbamate 667 g (3 mol) of di-tert-butyl dicarbonate are introduced into a 10 litre round-bottomed flask. 4.5 liters of a 2 M sodium hydroxide solution and 453 g (2.58 mol) of 3-bromoaniline are added under nitrogen. The mixture is heated under reflux for 4.5 hours. The reaction medium is extracted with ethyl acetate, the organic phase is washed with water and then evaporated under vacuum. The solid obtained is taken up, with stirring, in heptane. After filtration and drying, 609 g (86%) of tert-butyl (3-bromophenyl)carbamate are obtained in the form of a white powder.

(b) tert-butyl (3-bromophenyl)methylcarbamate 9.33 g (0.22 mol) of NaH at 60% in oil and 250 ml of DMF are introduced under nitrogen into a round-bottomed flask. 53 g (0.18 mol) of (3-bromophenyl)carbamic acid tert-butyl ester in solution in 150 ml of DMF are added dropwise. After 10 minutes, 14.5 ml (0.22 mmol) of methyl iodide are added dropwise. The mixture is stirred at room temperature for 30 minutes. After filtration of the NaI and evaporation of the DMF, the medium is solubilized in 350 ml of ethyl acetate and washed with twice 300 ml of water. After drying over sodium sulphate and evaporation of the solvents, 55 g (98%) of tert-butyl (3-bromophenyl)methylcarbamate are obtained in the form of a yellow liquid.

(c) tert-butyl (4'-formylbiphenyl-3-yl)methylcarbamate

In a manner similar to Example 1(c), by reacting 55 g (0.19 mol) of tert-butyl (3-bromophenyl)methylcarbamate with 50.5 g (0.30 mol) of 4-formylbenzeneboronic acid, 48 g (80%) of tert-butyl (4'-formylbiphenyl-3-yl)methylcarbamate are obtained after purification by chromatography on a silica column eluted with a heptane and ethyl acetate (90/10) mixture.

(d) tert-butyl [4'-(2,4dioxothiazolidin-5-ylidenemethyl)biphenyl-3-yl]methylcarbamate In a manner similar to Example 1(d), by reacting 40 g (0.128 mol) of tert-butyl (4'-formylbiphenyl-3-yl)methylcarbamate with 15 g (0.128 mol) of 2,4-thiazolidinedione and 3.7 g (0.025 mol) of piperidinium acetate and 0.4 l of toluene, 42.8 g (81.6%) of tert-butyl [4'-(2,4-dioxothiazolidin-5-ylidenemethyl)biphenyl-3-yl]methylcarbamate are obtained.

(e) tert-butyl [4'-(2,4-dioxothiazolidin-5-ylmethyl)biphenyl-3-yl]methylcarbamate 3.69 g (0.009 mol) of tert-butyl [4'-(2,4-dioxothiazolidin-5-ylidenemethyl)biphenyl-3-yl]methylcarbamate, 6 ml of THF and 7.3 ml of pyridine are introduced, in order, into a 50 ml three-necked round-bottomed flask. The mixture is placed under nitrogen and 10 ml of a freshly prepared 2 M LiBH$_4$ solution (0.02 mol) in THF are added dropwise. After stirring for 30 minutes at room temperature, the mixture is heated under reflux for 16 hours. The reaction medium is poured over 32 ml of a 1 N HCl solution and the THF is evaporated under vacuum. The precipitate obtained is filtered. After drying, the crude product (2.75 g) is chromatographed on 95 g of silica gel, eluting with a heptane/ethyl acetate=3/7 mixture. 2.45 g (66%) of tert-butyl [4'-(2,4-dioxothiazolidin-5-ylmethyl)biphenyl-3-yl]methylcarbamate are obtained.

(f) 5-(3'-methylaminobiphenyl-4-ylmethyl)thiazolidine-2,4-dione 2.32 g (5.6 mmol) of [4'-(2,4-dioxothiazolidin-5-ylmethyl)biphenyl-3-yl]methylcarbamic acid tert-butyl ester, 40 ml of dichloromethane and 6.4 g (56 mmol) of trichloroacetic acid are introduced into a 100 ml round-bottomed flask. After stirring for 24 h at room temperature, the reaction medium is concentrated in a rotary evaporator and taken up in diisopropyl ether. After trituration and stirring, it is filtered, taken up in 50 ml of water and neutralized with 0.53 g (6.2 mmol) of sodium bicarbonate. The precipitate is filtered, washed with ethyl ether and dried under vacuum. 1.43 g (81.7%) of 5-(3'-methylaminobiphenyl-4-ylmethyl)thiazolidine-2,4-dione are obtained in the form of a white powder.

(g) 1-[4'-(2,4-dioxothiazolidin-5-ylmethyl)biphenyl-3-yl]-3-(4-hexyloxyphenyl)-1-methylurea 0.67 g (2.14 mmol) of 5-(3'-methylaminobiphenyl-4-ylmethyl)thiazolidine-2,4-dione in 20 ml of dichloromethane is introduced into a 50 ml round-bottomed flask. 1 g (4.3 mmol) of 1-hexyloxy-4-isocyanatobenzene is added and the mixture is heated under reflux for 16 hours. The reaction medium is poured at room temperature over a 1 N HCl solution and extracted with ethyl acetate. The organic phase is washed with water and dried over magnesium sulphate. After evaporation of the solvents, the product obtained is purified by chromatography on silica gel (eluent: heptane/ethyl acetate=3/2). 0.78 g (68%) of 1-[4'-(2,4-dioxothiazolidin-5-ylmethyl)biphenyl-3-yl]-3-(4-hexyloxyphenyl)-1-methylurea is obtained in the form of a white powder having a melting point of 146–148° C.

$^1$H NMR (DMSO d6; 400 MHz): 0.81 (t, 3H); 1.29 (m, 4H); 1.39 (m, 2H); 1.67 (m, 2H); 3.18 (dd, J=9.6 Hz and J=14.1 Hz, 1H); 3.31 (s, 3H); 3.43 (dd, J=4.3 Hz and J=14.1 Hz, 1H); 3.90 (m, 2H); 4.96 (dd, J=4.3 Hz and J=9.6 Hz, 1H); 6.80 (m, 2H); 7.28–7.66 (m, 1OH); 8.07 (s, 1H); 12.10 (broad s, 1H).

EXAMPLE 35

Transactivation Test

The agonist activity towards the PPARγ receptors of the compounds according to the invention may be evaluated by transactivation tests.

The capacity of the molecules to activate and/or inhibit the PPARγ receptors is evaluated from Hela cells stably transfected with the chimeric Gal-PPARγ receptor (LBD).

96-well plates are inoculated at the rate of 10 000 cells/100 μl/well in DMEM 10% SDL medium and then placed for 24 hours at 37° C., 7% $CO_2$.

To determine the PPARγ agonist activity, the cells are then treated by addition of 5 μl/well of the molecules to be tested at the final concentration of 1 μM. Cells are also treated in parallel with a reference agonist, (−)-3-{4-[2-(benzooxazol-2-ylmethylamino)ethoxy]phenyl}-2-ethoxypropionic acid, 1 μM.

After another incubation of 24 hours at 37° C., 7% $CO_2$, a luciferase assay is carried out with the aid of the "Steady-Glo Luciferase Assay System" kit from Promega. The luminescence is counted on a Microbeta Trilux microplate reader (Wallac).

The agonist activity of the test product will be expressed as a percentage activation relative to the control agonist, the reference agonist at 1 μM.

By applying this same protocol with the chimeric Gal-PPARα receptor, it is possible to measure the agonist activity of the compounds towards the PPARalpha receptors and thus to compare it with that of the PPARγ receptor.

The AC50, expressed in nM, is determined as the concentration which makes it possible to obtain 50% activation of the basal signal relative to the reference agonist.

The results obtained for the compounds according to the invention are grouped together in the following table:

|  | % Activation (at 1 microM) |  | AC50 (in nM) |  |
|---|---|---|---|---|
|  | PPARα | PPARγ | PPARα | PPARγ |
| Compound of Example 2 | 13.7 | N.Y. | N.T | 55.5 |
| Compound of Example 3 | 22.3 | N.T. | >50 000.0 | 13.1 |
| Compound of Example 4 | 39.8 | N.T. | >50 000.0 | 24.2 |
| Compound of Example 5 | 26.6 | N.T. | >50 000.0 | 23.3 |
| Compound of Example 6 | 7.9 | N.T. | <50 000.0 | 4.0 |
| Compound of Example 7 | 37.8 | 97.2 | N.T. | 63.8 |
| Compound of Example 8 | 33.6 | 97.2 | N.T. | 307.3 |
| Compound of Example 9 | 4.3 | 105.9 | N.T. | 181.9 |
| Compound of Example 10 | 13.75 | 183.2 | >50 000.0 | 3.3 |
| Compound of Example 11 | 13.15 | 90.1 | >50 000.0 | 15.1 |
| Compound of Example 12 | 12.3 | 167.9 | >50 000.0 | 3.2 |
| Compound of Example 13 | 13.4 | 112.3 | >50 000.0 | 36.7 |
| Compound of Example 14 | 19.1 | 76.7 | N.T. | 142.8 |
| Compound of Example 15 | 28.8 | 101.6 | >50 000.0 | 5.0 |
| Compound of Example 16 | 22.9 | 93.3 | >50 000.0 | 0.55 |
| Compound of Example 17 | 15.1 | 96.1 | >50 000.0 | 3.8 |
| Compound of Example 18 | 37.3 | 90.7 | >50 000.0 | 42.5 |
| Compound of Example 19 | 100.2 | 102.1 | >50 000.0 | 2.9 |
| Compound of Example 20 | 41.9 | 113.5 | >50 000.0 | 7.7 |
| Compound of Example 21 | −4.2 | 104.2 | N.T. | 22 |
| Compound of Example 22 | −3.9 | 108.3 | N.T. | 4.2 |
| Compound of Example 23 | 11.9 | 90.0 | N.T. | 1.0 |

N.T. means not tested

These results show the transactivation activity of the compounds according to the invention. These results show more particularly the specificity of the activation of the compounds of the invention for the PPPR-γ subtype compared with the activation of the compounds for the PPAR-α subtype.

EXAMPLE 36

Binding Test

The affinity of the compounds of the invention for the human PPARγ receptor was determined in a test of binding, by competition for the attachment of a reference agonist, the following tritiated compound 5-{4-[2-(methylpyridin-2-ylamino)ethoxy]benzyl}thiazolidine-2,4-dione.

The receptors are obtained by infecting SF9 insect cells with a recombinant bacculovirus. They exist in the form of hPPARγ/RXRα heterodimers. The presence of RXRα increases the solubility and the stability of the hPPARγ receptor and, consequently, its biological activity, without as a result interfering in the determination of the binding constants.

The technique of adsorption on hydroxyapatite gel was used to separate the ligand bound to the receptor from the free ligand. The results are expressed as Kd value (nM) which represents the dissociation constant at equilibrium obtained for each compound.

The results obtained for the compounds according to the invention are grouped together in the following table:

|  | Binding to PPARγ Kd (in nM) |
|---|---|
| Compound of Example 3 | 375.0 |
| Compound of Example 4 | 250.0 |
| Compound of Example 5 | 500.0 |
| Compound of Example 6 | 60.0 |
| Compound of Example 10 | 60.0 |
| Compound of Example 11 | 375.0 |
| Compound of Example 12 | 60.0 |
| Compound of Example 13 | 500.0 |
| Compound of Example 15 | 60.0 |
| Compound of Example 16 | 4.0 |
| Compound of Example 17 | 15.0 |
| Compound of Example 19 | 8.0 |
| Compound of Example 20 | 9.5 |

These results show the very good affinity of the compounds according to the present invention for the PPARγ receptor.

EXAMPLE 37

Various concrete formulations based on the compounds according to the invention have been illustrated in this example.

A-ORAL ROUTE
(a) 0.2 g tablet

| Compound of Example 16 | 0.001 g |
|---|---|
| Starch | 0.114 g |
| Bicalcium phosphate | 0.020 g |
| Silica | 0.020 g |
| Lactose | 0.030 g |
| Talc | 0.010 g |
| Magnesium stearate | 0.005 g |

(b) Oral suspension in 5 ml vials

| Compound of Example 17 | 0.001 g |
|---|---|
| Glycerine | 0.500 g |
| Sorbitol at 70% | 0.500 g |
| Sodium saccharinate | 0.010 g |
| Methyl para-hydroxybenzoate | 0.040 g |
| Flavouring | qs |
| Purified water | qs 5 ml |

(c) 0.8 g tablet

| Compound of Example 19 | 0.500 g |
|---|---|
| Pregelatinized starch | 0.100 g |
| Microcrystalline cellulose | 0.115 g |
| Lactose | 0.075 g |
| Magnesium stearate | 0.010 g |

(d) Oral suspension in 10 ml vials

| Compound of Example 20 | 0.200 g |
|---|---|
| Glycerine | 1.000 g |
| Sorbitol at 70% | 1.000 g |
| Sodium saccharinate | 0.010 g |
| Methyl para-hydroxybenzoate | 0.080 g |
| Flavouring | qs |
| Purified water | qs 10 ml |

B-TOPICAL ROUTE
(a) Salve

| Compound of Example 12 | 0.020 g |
|---|---|
| Isopropyl myristate | 81.700 g |
| Fluid liquid paraffin | 9.100 g |
| Silica ("Aerosil 200" sold by DEGUSSA) | 9.180 g |

(b) Salve

| Compound of Example 15 | 0.300 g |
|---|---|
| Petroleum jelly | qs 100 g |

(c) Nonionic water-in-oil cream

| Compound of Example 10 | 0.100 g |
|---|---|
| Mixture of emulsifying lanolin alcohols, waxes and oils ("anhydrous eucerin" sold by BDF) | 39.900 g |
| Methyl para-hydroxybenzoate | 0.075 g |
| Propyl para-hydroxybenzoate | 0.075 g |
| Sterile demineralized water | qs 100 g |

(d) Lotion

| Compound of Example 19 | 0.100 g |
|---|---|
| Polyethylene glycol (PEG 400) | 69.900 g |
| Ethanol at 95% | 30.000 g |

(e) Hydrophobic salve

| Compound of Example 20 | 0.300 g |
|---|---|
| Isopropyl myristate | 36.400 g |
| Silicon oil ("Rhodorsil 47 V 300" sold by RHONE-POULENC) | 36.400 g |
| Beeswax | 13.600 g |
| Silicone oil ("Abil 300,000 cst" sold by GOLDSCHMIDT) | qs 100 g |

(f) Nonionic oil-in-water cream

| Compound of Example 16 | 1.000 g |
|---|---|
| Cetyl alcohol | 4.000 g |
| Glyceryl monostearate | 2.500 g |
| PEG 50 stearate | 2.500 g |
| Shea butter | 9.200 g |
| Propylene glycol | 2.000 g |
| Methyl para-hydroxybenzoate | 0.075 g |
| Propyl para-hydroxybenzoate | 0.075 g |
| Sterile demineralized water | qs 100 g |

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A compound of the formula (I):

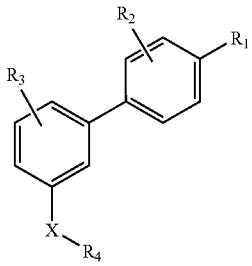

in which $R_1$ is a radical of the following formula:

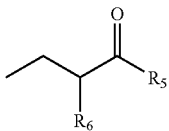

wherein $R_5$ and $R_6$ are as defined below; $R_2$ and $R_3$, which may be identical or different, are each a hydrogen atom, an alkyl radical having from 1 to 6 carbon atoms, an aryl radical, a halogen atom, a radical —$OR_7$, a polyether radical, a nitro group or an amino group which may be optionally substituted with alkyl radicals having from 1 to 6 carbon atoms, wherein $R_7$ is as defined below; X is one of the radicals having the following structures:

—$CH_2$—$N(R_8)$—CO—

—$N(R_8)$—CO—$N(R_9)$—

—$N(R_8)$—CO—$CH_2$—

—$N(R_8)$—$CH_2$—CO— whether read from left to right or vise versa, wherein $R_8$ and $R_9$ are as defined below; $R_4$ is a phenyl, benzyl, phenethyl, thienyl, furyl or pyridyl radical, each of these radicals being substituted with a group $R_{10}$, wherein $R_{10}$ is as defined below, a pyrrolyl, pyrazinyl, naphthyl, biphenyl, indolyl, indenyl, benzothienyl, benzofuryl, benzothiazolyl or quinolyl radical, with the proviso that each of these radicals may be mono- or disubstituted with a group $R_{11}$ and/or $R_{12}$, wherein $R_{11}$ and $R_{12}$ are as defined below, a radical —$(CH_2)$n-$(CO)_q R_{13}$, wherein n, q and $R_{13}$ are as defined below, an adamantyl, diphenylmethyl, diphenylethyl, diphenylpropyl, diphenylbutyl, cyclopropylmethyl, cyclopentylethyl, 2-benzimidazolyl-ethyl, cyclohexylmethyl, phenoxyphenyl, 9H-fluorenyl, benzyloxyphenyl, 4-heptyloxyphenyl, or 4-(6-methyl-2-benzothiazolyl)phenyl radical, or a radical —$(CH_2)$n-O—$R_{13}$, wherein n and $R_{13}$ are as defined below; $R_5$ is a hydroxyl group or an alkoxy radical having from 1 to 9 carbon atoms; $R_6$ is an alkyl radical having from 1 to 6 carbon atoms, a radical $OR_{14}$ or a radical $SR_{14}$, wherein $R_{14}$ is as defined below; $R_7$ is a hydrogen atom, an alkyl radical having from 1 to 6 carbon atoms, an aryl radical or an aralkyl radical; $R_8$ is a hydrogen atom or an alkyl radical having from 1 to 6 carbon atoms; $R_9$ is a hydrogen atom or an alkyl radical having from 1 to 6 carbon atoms; $R_{10}$ is a radical —$S(O)_m R_{15}$, a radical —$(CH_2)$p-$COR_{16}$, or a radical —O—$R_{17}$, wherein m, p, $R_{15}$, $R_{16}$ and $R_{17}$ are as defined below; $R_{11}$ and $R_{12}$ are each a halogen atom, a radical $CF_3$, an alkyl radical having from 1 to 12 carbon atoms, an alkoxy radical having from 1 to 9 carbon atoms, a polyether radical, a nitro functional group, a hydroxyl group optionally protected by an acetyl or benzoyl group, an amino functional group optionally substituted with at least one alkyl radical having from 1 to 12 carbon atoms or with a radical —CONH—$R_{24}$, or protected by an acetyl or benzoyl group, a radical —$S(O)_m R_{15}$, a radical $(CH_2)$p-$COR_{16}$ or a radical —$OR_{17}$, wherein m, p, $R_{15}$, $R_{16}$, $R_{17}$ and $R_{24}$ are as defined below; n is a number ranging from 1 to 9; q is 0 or 1; $R_{13}$ is a radical —$OR_{18}$, a radical —$N(R_{19})(R_{20})$, an aryl radical, an aralkyl radical or a heteroaryl radical, wherein $R_{18}$, $R_{19}$ and $R_{20}$ are as defined below; m is 0, 1 or 2; p is 0, 1 or 2; $R_{14}$ is an alkyl radical having from 1 to 12 carbon atoms, a radical $CF_3$, an aryl radical or an aralkyl radical; $R_{15}$ is an alkyl radical having from 1 to 12 carbon atoms, an aryl radical or an aralkyl radical; $R_{16}$ is an alkyl radical having from 1 to 12 carbon atoms, a radical —$OR_{21}$, a radical —$N(R_{22})(R_{23})$, an aryl radical or an aralkyl radical, wherein $R_{21}$, $R_{22}$ and $R_{23}$ are as defined below; $R_{17}$ is an aryl radical or an aralkyl radical; $R_{18}$ is a hydrogen atom or an alkyl radical having from 1 to 12 carbon atoms; $R_{19}$ and $R_{20}$, which may be identical or different, are each a hydrogen atom, an alkyl radical having from 1 to 12 carbon atoms, or may together form a heterocycle; $R_{21}$ is a hydrogen atom or an alkyl radical having from 1 to 12 carbon atoms; $R_{22}$ and $R_{23}$, which may be identical or different, are each a hydrogen atom, an alkyl radical having from 1 to 12 carbon atoms, or may together form a heterocycle; $R_{24}$ is a phenyl, diphenylmethyl, diphenylpropyl, diphenylbutyl, biphenylyl, phenoxyphenyl, 9H-fluorenyl, 4-benzyloxyphenyl, 4-heptyloxyphenyl, or 4-(6-methyl-2-benzothiazolyl)phenyl radical; or a salt of a compound of formula (I) when $R_1$ contains a carboxylic acid functional group; and the optical and geometric isomers of said compounds of formula (I).

2. A compound as defined by claim 1, comprising a salt of an alkali or alkaline earth metal, a zinc salt, or a salt of an organic amine.

3. A compound as defined by claim 1, wherein $R_2$, $R_3$, $R_4$, or X of formula (I) comprises at least one alkyl radical having from 1 to 6 carbon atoms selected from methyl, ethyl, isopropyl, butyl, tert-butyl and hexyl radicals.

4. A compound as defined by claim 1, wherein $R_2$, $R_3$, $R_4$, or X of formula (I) comprises at least one alkyl radical having from 1 to 12 carbon atoms selected from methyl, ethyl, isopropyl, butyl, tert-butyl, hexyl, octyl, decyl and dodecyl radicals.

5. A compound as defined by claim 1, wherein $R_2$, $R_3$, $R_4$, or X of formula (I) comprises at least one polyether radical having from 1 to 6 carbon atoms interrupted by at least one oxygen atom.

6. A compound as defined by claim 1, wherein $R_2$, $R_3$, $R_4$, or X of formula (I) comprises at least one fluorine, chlorine or bromine atom.

7. A compound as defined by claim 1, wherein $R_2$, $R_3$, $R_4$, or X of formula (I) comprises at least one alkoxy radical having from 1 to 9 carbon atoms selected from methoxy, ethoxy, isopropyloxy, tert-butoxy and hexyloxy radicals.

8. A compound as defined by claim 1, wherein $R_2$, $R_3$, $R_4$, or X of formula (I) comprises at least one aryl radical which is a phenyl or naphthyl radical which may be mono- or disubstituted with a halogen atom, a radical CF3, an alkyl radical having from 1 to 12 carbon atoms, an alkoxy radical having from 1 to 6 carbon atoms, a nitro functional group, a polyether radical, a hydroxyl group optionally protected by an acetyl or benzoyl group or an amino functional group optionally protected by an acetyl or benzoyl group or optionally substituted with at least one alkyl radical having from 1 to 12 carbon atoms.

9. A compound as defined by claim 1, wherein $R_2$, $R_3$, $R_4$, or X of formula (I) comprises at least one aralkyl radical which is a benzyl or phenethyl radical which may be mono- or disubstituted with a halogen atom, a radical CF3, an alkyl radical having from 1 to 12 carbon atoms, an alkoxy radical having from 1 to 6 carbon atoms, a nitro functional group, a polyether radical, a hydroxyl group optionally protected by an acetyl or benzoyl group or an amino functional group optionally protected by an acetyl or benzoyl group or optionally substituted with at least one alkyl radical having from 1 to 12 carbon atoms.

10. A compound as defined by claim 1, wherein $R_2$, $R_3$, $R_4$, or X of formula (I) comprises at least one heteroaryl radical which is a pyridyl, furyl, thienyl or isoxazolyl radical, optionally substituted with at least one halogen atom, an alkyl radical having from 1 to 12 carbon atoms, an alkoxy radical having from 1 to 6 carbon atoms, a nitro functional group, a polyether radical, a hydroxyl radical optionally protected by an acetyl or benzoyl group or an amino functional group optionally protected by an acetyl or benzoyl group or optionally substituted with at least one alkyl radical having from 1 to 12 carbon atoms.

11. A compound as defined by claim 1, comprising at least one heterocycle which is a piperidino, morpholino, pyrrolidino or piperazino radical optionally substituted with an alkyl radical having from 1 to 12 carbon atoms.

12. A compound as defined by claim 1, comprising:
(S)-3-(3'-{[(1-biphenyl-4-ylmethanoyl)methyl-amino]methyl}biphenyl-4-yl)-2-ethoxypropionic acid;
(S)-2-ethoxy-3-(3'-{[methyl-(6-oxo-6-phenylhexanoyl)amino]methyl}biphenyl-4-yl)propionic acid; or
(S)-2-ethoxy-3-{3'-[({1-[6-(2-methoxyethoxy-methoxy)naphthalen-2-yl]methanoyl}methylamino)methyl]-biphenyl-4-yl}propionic acid;
or mixture thereof.

13. A compound as defined by claim 1, wherein $R_5$ is a hydroxyl group and $R_6$ is the radical $OR_{14}$ and/or X is a radical having the structure —$CH_2$—$N(R_8)$—CO— or —$N(R_8)$—CO—$N(R_9)$— read from left to right or vise versa.

14. A pharmaceutical composition comprising at least one compound as defined in claim 1, formulated into a physiologically acceptable carrier therefor.

15. A composition as defined by claim 14, comprising from 0.001% to 10% by weight relative to the total weight of the composition of said at least one compound.

16. A composition according to claim 14, comprising from 0.01% to 1% by weight relative to the total weight of the composition of said at least one compound.

17. A cosmetic composition comprising at least one compound as defined in claim 1, formulated into a cosmetically acceptable carrier therefor.

18. The composition as defined by claim 17, comprising from 0.001% to 3% by weight relative to the total weight of the composition of said at least one compound.

* * * * *